United States Patent [19]

Möller et al.

[11] 4,113,957
[45] Sep. 12, 1978

[54] 1-SUBSTITUTED PYRAZOLES

[75] Inventors: Eike Möller, Wuppertal, Germany; Karl-August Meng, deceased, late of Wuppertal, Germany, by Ilse Heide Frieda Meng, heir; Egbert Wehinger, Neviges, Germany; Harald Horstmann, Wuppertal, Germany; Friedel Seuter, Neviges, Germany

[73] Assignee: Bayer Aktiengesellschaft, Germany

[21] Appl. No.: 693,971

[22] Filed: Jun. 8, 1976

[30] Foreign Application Priority Data

Jun. 13, 1975 [DE] Fed. Rep. of Germany ....... 2526469

[51] Int. Cl.$^2$ .......................................... C07D 231/20
[52] U.S. Cl. .......................... 548/377; 260/294.8 G; 260/293.7; 260/295 R; 260/295.5 R; 260/306.8 D; 260/306.8 R; 260/307 H; 260/307 R; 542/468; 542/470; 544/238; 544/364; 544/371; 544/405; 544/333
[58] Field of Search ............ 260/310 R, 310 A, 293.7, 260/375; 548/374, 377

[56] References Cited

U.S. PATENT DOCUMENTS 2,681,915  6/1954  Gysin et al. ............... 260/310 R
3,190,888  6/1965  Wolf et al. ................. 260/310 R

FOREIGN PATENT DOCUMENTS 961,037  8/1961  United Kingdom ............... 260/310 A Primary Examiner—Natalie Trousof
Assistant Examiner—Jane T. Fan
Attorney, Agent, or Firm—Jacobs & Jacobs

[57] ABSTRACT

Pyrazoles of the formula

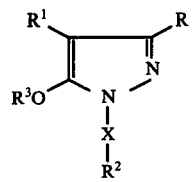

wherein
R is hydrogen, alkyl, trifluoromethyl, aryl, aralkyl or a heterocycle;
$R^1$ is hydrogen, alkyl, aryl or aralkyl;
$R^3$ is an unsubstituted or substituted carboacyl or sulphonyl moiety;
X is (a) methylene; (b) ethylene; (c) ethylene wherein 1 hydrogen atom on one or both of the carbon atoms is substituted by alkyl of 1 to 4 carbon atoms; (d) ethylene, or ethylene wherein 1 hydrogen atom on one or both of the carbon atoms is substituted by alkyl of 1 to 4 carbon atoms, linked to $R^2$ via an oxygen or sulphur atom; (e) propenyl; of (f) propenyl wherein a hydrogen atom on 1, 2 or 3 of the carbon atoms is substituted by alkyl of 1 to 4 carbon atoms; said propenyl moiety being linked to the $N^1$ atom via a methylene moiety; and
$R^2$ is aryl unsubstituted or substituted by 1 or 2 of the same or different substituents selected from the group consisting of alkyl, alkenyl, alkoxy, halo, trifluoromethyl, trifluoromethoxy, cycloalkyl, cycloalkenyl, mono- or di-alkylamino, nitro, cyano, unsubstituted or substituted carboxamido, unsubstituted or substituted sulphonamido and SO$_n$-alkyl wherein n is 0 to 2, or aryl having 2 substituents which together form a branched or unbranched, saturated or unsaturated 5- to 7-membered isocyclic or heterocyclic ring, said heterocyclic ring containing 1 or 2 oxygen or sulphur atoms, or pyridyl;

are useful for their diuretic, saluretic, antihypertensive and antithrombotic properties.

14 Claims, No Drawings

1-SUBSTITUTED PYRAZOLES

The present invention is concerned with pyrazoles, processes for their production, pharmaceutical compositions wherein said compounds are the active agents and to methods of effecting diuresis and saluresis in humans and animals, treating hypertension in humans and animals and treating thromboses in humans and animals utilizing said compounds.

It is known that pyrazole derivatives are useful as antipyretics, analgesics and antiphlogistics (see G. Erhart and H. Ruschig, Arzneimittel [Medicaments], Volume 1, page 148 (1972).

In U.S. Ser. Nos. 521,906; 638,517; 637,861; 515,448; 459,467; 610,150; 459,408; 633,601; 633,636; 461,282; 540,972; 540,815; 579,825; 633,396; 633,647; 461,285; 543,664; 578,516; 631,946; 632,165; 532,311; 619,891; and 582,773; pyrazolones and pyrazoles are disclosed which are useful for their diuretic, saluretic and antihypertensive properties. The compounds of the present invention differ structurally from the compounds of said applications; in particular, by the nature of the 5-position substituent, and, in part, by the nature of the group which links the 1-position ring nitrogen with the substituent at the 1-position.

More particularly, the present invention is concerned with pyrazoles of the formula

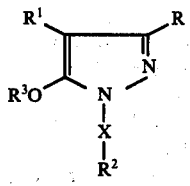

wherein
- R is hydrogen, alkyl, trifluoromethyl, aryl, aralkyl or a heterocycle;
- $R^1$ is hydrogen, alkyl, aryl or aralkyl;
- $R^3$ is an unsubstituted or substituted carboacyl or sulphonyl moiety;
- X is (a) methylene; (b) ethylene; (c) ethylene wherein 1 hydrogen atom on one or both of the carbon atoms is substituted by alkyl of 1 to 4 carbon atoms; (d) ethylene, or ethylene wherein 1 hydrogen atom on one or both of the carbon atoms is substituted by alkyl of 1 to 4 carbon atoms, linked to $R^2$ via an oxygen or sulphur atom; (e) propenyl; or (f) propenyl wherein a hydrogen atom on 1, 2 or 3 of the carbon atoms is substituted by alkyl of 1 to 4 carbon atoms; said propenyl moiety being linked to the $N^1$ atom via a methylene moiety; and
- $R^2$ is aryl unsubstituted or substituted by 1 or 2 of the same or different substituents selected from the group consisting of alkyl, alkenyl, alkoxy, halo, trifluoromethyl, trifluoromethoxy, cycloalkyl, cycloalkenyl, mono- or di-alkylamino, nitro, cyano, unsubstituted or substituted carboxamido, unsubstituted or substituted sulphonamido and $SO_n$-alkyl wherein n is 0 to 2, or aryl having 2 substituents which together form a branched or unbranched, saturated or unsaturated 5- to 7-membered isocyclic or heterocyclic ring, said heterocyclic ring containing 1 or 2 oxygen or sulphur atoms, or pyridyl.

If X in formula (I) contains an asymmetric carbon atom, the racemate can, of course, be resolved into the optical antipodes. Either the racemate or the antipodes can be administered as the active agent.

The pyrazoles of formula (I) of the present invention are produced when 5-pyrazolone derivatives of the formula

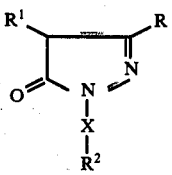

wherein R, $R^1$, X and $R^2$ are as above defined, are reacted with acid derivatives, preferably with carboxylic acid or carbonic acid derivatives which contain the appropriate unsubstituted or substituted carboacyl moiety or with a sulphonic acid derivative which contains the appropriate substituted or unsubstituted sulphonyl moiety. These may be represented by the formula

wherein A is a moiety which is eliminated under the conditions of the reaction, such as halo, a 5-membered heterocyclic azole ring, an alkyl moiety which is bonded to the carbonyl carbon atom via an oxygen or sulphur atom or a phenyl moiety unsubstituted or substituted by 1 or 2 nitro moieties or an acyloxy moiety; and Y is $R^6$ wherein $R^6$ is as below defined; or by the formula

wherein A' is halo; and Z is $R^7$ wherein $R^7$ is as below defined; either in the presence or absence of inert organic solvents and basic materials such as alkali metal hydroxides and carbonates or alkaline earth metal hydroxides and carbonates or organic bases such as triethylamine or pyridine, at a temperature of from about $-20°$ C to $+150°$ C.

The optical antipodes of the compounds according to the present invention are prepared in accordance with methods known from the literature (compare, for example, Houben-Weyl, IV/2, pages 509 et seq.) by interaction of the compound according to the present invention with a chiral medium such as, for example, by recrystallization from an optically active solvent or by chromatography on a chiral carrier substance or by reaction of the optically pure 5-pyrazolone derivatives of the formula (II) with the appropriate carboxylic acid derivatives, carbonic acid derivatives or sulphonic acid derivatives of the formulae (III) and (IV).

According to one embodiment of the present invention

R is hydrogen; lower alkyl; trifluoromethyl; aryl of 6 to 10 carbon atoms unsubstituted or substituted by 1 to 3 substituents selected from the group consisting of alkyl of 1 to 4 carbon atoms, alkenyl of 2 to 4 carbon atoms, alkoxy of 1 to 4 carbon atoms, cycloalkyl of 5 to 7 carbon atoms, cycloalkkenyl of 5 to 7 carbon atoms, halo, trifluoromethyl, trifluoromethoxy, nitro and phenyl; aralkyl of 6 to 10 carbon atoms in the aryl moiety and 1 to 4 carbon atoms in the alkyl moiety unsubstituted or nuclear substituted by 1 or 2 substituents selected from the group consisting of alkyl of 1 to 4 carbon atoms, alkenyl of 2 to 4 carbon atoms, alkoxy of 1 to 4 carbon atoms, cycloalkyl of 5 to 7 carbon atoms, cycloalkenyl of 5 to 7 carbon atoms, halo, trifluoromethyl, trifluoromethoxy, nitro and phenyl; or pyridyl;

$R^1$ is hydrogen; lower alkyl; aryl of 6 to 10 carbon atoms unsubstituted or substituted by 1 or 2 substituents selected from the group consisting of alkyl of 1 to 4 carbon atoms, alkenyl of 2 to 4 carbon atoms, alkkoxy of 1 to 4 carbon atoms, cycloalkyl of 5 to 7 carbon atoms, cycloalkenyl of 5 to 7 carbon atoms, halo, trifluoromethyl, trifluoromethoxy, nitro and phenyl; or aralkyl of 6 to 10 carbon atoms in the aryl moiety and 1 to 4 carbon atoms in the alkyl moiety;

$R^3$ is $R^6CO$ wherein $R^6$ is lower alkyl; lower alkyl substituted by phenoxy; lower alkoxy; haloalkyl of 1 to 4 carbon atoms in the alkyl moiety and 1 to 3 halo atoms; cycloalkyl of 5 to 7 carbon atoms; lower alkylthio;haloalkoxy of 1 to 4 carbon atoms in the alkoxy moiety and 1 to 3 halo atoms; haloalkylthio of 1 to 4 carbon atoms in the alkyl moiety and 1 to 3 halo atoms; lower alkoxy (lower alkyl); mono- or dilower alkylamino (lower alkyl); phenyl unsubstituted or substituted by 1 to 3 substituents selected from the group consisting of alkyl of 1 to 4 carbon atoms, alkoxy of 1 to 4 carbon atoms, halo, trifluoromethyl, trifluoromethoxy, nitro, cyano, $SO_n$-alkyl of 1 to 4 carbon atoms in the alkyl moiety and n is 0 to 2, $SO_n$-$CF_3$ wherein n is 0 to 2, carbonamido and sulphonamido; phenyl having fused thereto a 5- to 7-membered heterocyclic ring having 1 or 2 oxygen or sulphur atoms; or a 5- to 7 -membered heterocyclic ring unsubstituted or substituted by alkyl of 1 to 4 carbon atoms, halo or nitro; or $R^7SO_2$ wherein $R^7$ is lower alkyl; cycloalkyl of 5 to 7 carbon atoms; or phenyl substituted by 1 or 2 substituents selected from the group consisting of alkyl of 1 to 4 carbon atoms, halo, trifluoromethyl, trifluoromethoxy, nitro, cyano and trifluroromethylsulphonyl;

X is (a) methylene; (b) ethylene; (c) ethylene wherein 1 hydrogen atom on one or both of the carbon atoms is substituted by alkyl of 1 to 4 carbon atoms; (d) ethylene, or ethylene wherein 1 hydrogen atom on one or both of the carbon atoms is substituted by alkyl of 1 to 4 carbon atoms, linked to $R^2$ via an oxygen or sulphur atom; (e) propenyl; or (f) propenyl wherein a hydrogen atom on 1, 2 or 3 of the carbon atoms is substituted by alkyl of 1 to 4 carbon atoms; said propenyl moiety being linked to the $N^1$ atom via a methylene moiety; and $R^2$ is aryl of 6 to 10 carbon atoms unsubstituted $R^6$ is alkyl of 1 to 4 carbon atoms; alkyl with 1 to 4 carbon atoms substituted by phenoxy; alkoxy of 1 to 4 carbon atoms; haloalkyl of 1 to 4 carbon trifluoromethoxy, cycloalkyl of 5 to 7 carbon atoms, cycloalkenyl of 5 to 7 carbon atoms, nitro, cyano, carboxamido unsubstituted or substituted by 1 or 2 alkyl moieties of 1 to 4 carbon atoms, or by 2 alkylene moieties of 1 to 4 carbon atoms which together with the nitrogen atom form a 5- to 7-membered heterocyclic ring, said ring having the ring nitrogen as the only heteroatom or said ring additionally having oxygen as a heteroatom, sulphonamido unsubstituted or substituted by 1 or 2 alkyl moieties of 1 to 4 carbon atoms or by 2 alkylene moieties of 1 to 4 carbon atoms which together with the nitrogen atom form a 5- to 7-membered heterocyclic ring, said ring having the ring nitrogen as the only heteroatom or said ring additionally having oxygen as a heteroatom, and $SO_n$-(lower alkyl) wherein n is 0 to 2; phenyl having fused thereto a saturated or unsaturated 5- to 7-membered isocyclic or heterocyclic ring, said heterocyclic ring containing 1 or 2 oxygen or sulphur heteroatoms; or pyridyl.

According to another embodiment of the present invention

R is hydrogen; alkyl of 1 to 4 carbon atoms; trifluoromethyl; phenyl unsubstituted or substituted by 1 to 3 substituents selected from the group consisting of alkyl of 1 to 4 carbon atoms, alkenyl of 2 to 4 carbon atoms, alkoxy of 1 to 4 carbon atoms, fluoro, chloro, bromo, trifluoromethyl, trifluoromethoxy and nitro, of by 1 or 2 substituents selected from the group consisting of cycloalkyl of 5 to 7 carbon atoms, cycloalkenyl of 5 to 7 carbon atoms and phenyl; benzyl unsubstituted or nuclear substituted by 1 or 2 substituents selected from the group consisting of alkyl of 1 to 4 carbon atoms, alkenyl of 2 to 4 carbon atoms, alkoxy of 1 to 4 carbon atoms, fluoro, chloro, bromo, trifluoromethyl, trifluoromethoxy and nitro, or by 1 or 2 substituents selected from the group consisting of cycloalkyl of 5 to 7 carbon atoms, cycloalkenyl of 5 to 7 carbon atoms and phenyl; or pyridyl;

$R^1$ is hydrogen; alkyl of 1 to 4 carbon atoms; phenyl unsubstituted or substituted by 1 or 2 substituents selected from the group consisting of alkyl of 1 to 4 carbon atoms, alkenyl of 2 to 4 carbon atoms, alkoxy of 1 to 4 carbon atoms, cycloalkyl of 5 to 7 carbon atoms, cycloalkenyl of 5 to 7 carbon atoms, fluoro, chloro, bromo, trifluoromethyl, trifluoromethoxy, nitro and phenyl; or benzyl; and $R^3$ is $R^6CO$ wherein $R^6$ is alkyl of 1 to 4 carbon atoms; phenoxyalkyl with 1 to 4 carbon atoms; haloalkyl of 1 to 4 carbon to 4 carbon atoms; haloalkyl of 1 to 4 carbon atoms in the alkyl moiety and 1 to 3 halo atoms; cycloalkyl of 5 to 7 carbon atoms; alkylthio of 1 to 4 carbon atoms; haloalkoxy of 1 to 4 carbon atoms in the alkyl moiety and 1 to 3 halo atoms; haloalkylthio of 1 to 4 carbon atoms in the alkyl moiety and 1 to 3 halo atoms; alkoxyalkyl of 1 to 4 carbon atoms in both moieties; mono- or di-alkylaminoalkyl of 1 or 2 carbon atoms in each alkyl moiety; or phenyl unsubstituted or substituted by 1 or 2 substituents selected from the group consisting of alkyl of 1 to 4 carbon atoms, alkoxy of 1 to 4 carbon atoms, fluoro, chloro, bromo, trifluoromethyl, trifluoromethoxy, $SO_n$-alkyl of 1 to 4 carbon atoms in the alkyl moiety and n is 0 to 2 and $SO_n$—$CF_3$ wherein n is 0 to 2.

According to another embodiment of the present invention

R is hydrogen; alkyl of 1 to 4 carbon atoms; trifluoromethyl; phenyl unsubstituted or substituted by 1 to 3 substituents selected from the group consisting of alkyl of 1 to 4 carbon atoms, alkenyl of 2 to 4 carbon atoms, alkoxy of 1 to 4 carbon atoms, cycloalkyl of 5 to 7 carbon atoms, cycloalkenyl of 5 to 7 carbon atoms, halo, trifluoromethyl, trifluoromethoxy, nitro and phenyl; benzyl unsubstituted or nuclear substituted by 1 or 2 substituents selected from the group consisting of alkyl of 1 to 4 carbon atoms, alkenyl of 2 to 4 carbon atoms, alkoxy of 1 to 4 carbon atoms, cycloalkyl of 5 to 7 carbon atoms, cycloalkenyl of 5 to 7 carbon atoms, halo, trifluoromethyl, trifluoromethoxy, nitro and phenyl; or pyridyl;

$R^1$ is hydrogen; alkyl of 1 to 4 carbon atoms; or phenyl unsubstituted or substituted by 1 or 2 substituents selected from the group consisting of alkyl of 1 to 4 carbon atoms, alkenyl of 2 to 4 carbon atoms, alkoxy of 1 to 4 carbon atoms, cycloalkyl of 5 to 7 carbon atoms, cycloalkenyl of 5 to 7 carbon atoms, halo, trifluoromethyl, trifluoromethoxy, nitro and phenyl; and $R^2$ is phenyl substituted by 1 or 2 substituents selected from the group consisting of alkyl of 1 of 6 carbon atoms, alkenyl of 2 to 6 carbon atoms, alkoxy of 1 to 6 carbon atoms, cycloalkyl of 5 to 7 carbon atoms, cycloalkenyl of 5 to 7 carbon atoms, halo, trifluoromethyl, trifluoromethoxy, nitro, cyano, dialkylamino of 1 to 4 carbon atoms in each alkyl moiety, carboxamido unsubstituted or substituted by 1 or 2 alkyl moieties of 1 to 4 carbon atoms or by 2 alkylene moieties of 1 to 4 carbon atoms which together with the nitrogen atom form a 5- to 7-membered heterocyclic ring, said ring having the ring nitrogen as the only heteroatom or said ring additionally having oxygen as a heteroatom, sulphonamido unsubstituted or substituted by 1 or 2 alkyl moieties of 1 to 4 carbon atoms or by 2 alkylene moieties of 1 to 4 carbon atoms which together with the nitrogen atom form a 5- to 7-membered heterocyclic ring, said ring having the ring nitrogen as the only heteroatom or said ring additionally having oxygen as a heteroatom, and $SO_n$-alkyl of 1 to 4 carbon atoms in the alkyl moiety and n is 0 to 2; phenyl having fused thereto a saturated or unsaturated, 5- to 7-membered isocyclic or heterocyclic ring, said heterocyclic ring having oxygen or sulphur as a heteroatom; naphthyl; or pyridyl.

According to another embodiment of the present invention $R^2$ is phenyl substituted by 1 or 2 substituents selected from the group consisting of methyl, fluoro, chloro and trifluoromethyl; tetramethylenephenyl; or naphthyl.

According to another embodiment of the present invention

R is hydrogen; alkyl of 1 to 4 carbon atoms, trifluoromethyl; phenyl; or benzyl;

$R^1$ is hydrogen; alkyl of 1 to 4 carbon atoms; or phenyl unsubstituted or substituted by alkyl of 1 or 2 carbon atoms, alkoxy of 1 or 2 carbon atoms, chloro, fluoro, trifluoromethyl or nitro;

$R^3$ is lower alkyl carbonyl; lower alkoxy carbonyl; benzoyl unsubstituted or nuclear substituted by 1 or 2 substituents selected from the group consisting of alkyl of 1 to 4 carbon atoms, alkoxy of 1 to 4 carbon atoms, chloro, fluoro, trifluoromethyl, nitro and cyano; phenoxyalkyl carbonyl of 1 to 4 carbon atoms in the alkyl moiety; furylcarbonyl; methylsulfonyl; or phenylsulphonyl substituted by alkyl of 1 to 4 carbon atoms or halo;

X is methylene or oxyethylene; and $R^2$ is phenyl unsubstituted or substituted by alkyl of 1 to 4 carbon atoms or halo.

According to another embodiment of the present invention

R is hydrogen; methyl; ethyl; propyl; trifluoromethyl; phenyl; or benzyl;

$R^1$ is hydrogen; methyl; or phenyl unsubstituted or substituted by methyl, methoxy, chloro, fluoro, trifluoromethyl or nitro;

$R^3$ is acetyl; ethoxycarbonyl; benzoyl unsubstituted or nuclear substituted by 1 or 2 substituents selected from the group consisting of methyl, methoxy, chloro, fluoro, trifluoromethyl, nitro and cyano; phenoxybutyryl; furylcarbonyl; methylsulphonyl; or phenylsulphonyl substituted by methyl or halo;

X is methylene or oxyethylene; and $R^2$ is phenyl unsubstituted or substituted by methyl or halo.

According to another embodiment of the present invention

R is alkyl of 1 to 4 carbon atoms; trifluoromethyl; or phenyl;

$R^1$ is hydrogen; alkyl of 1 to 4 carbon atoms; phenyl; or halophenyl;

$R^3$ is alkylcarbonyl of 1 to 6 carbon atoms in the alkyl moiety; phenoxyalkylcarbonyl of 1 to 6 carbon atoms in the alkyl moiety; alkoxycarbonyl of 1 to 6 carbon atoms in the alkoxy moiety; haloalkylcarbonyl of 1 to 6 carbon atoms in the alkyl moiety and 1 to 3 halo atoms; alkoxyalkylcarbonyl of 1 to 6 carbon atoms in the alkoxy and alkyl moieties; benzoyl nuclear substituted by 1 or 2 substituents selected from the group consisting of alkyl of 1 to 4 carbon atoms, halo, trifluoromethyl, trifluoromethoxy and nitro, or by 1 trifluoromethylsulphonyl; dialkylaminoalkylcarbonyl of 1 to 4 carbon atoms in each of the alkyl moieties; pyrrylcarbonyl; thienylcarbonyl; halothienylcarbonyl; furylcarbonyl; halofurylcarbonyl; pyrazolylcarbonyl; alkylpyrazolylcarbonyl of 1 to 4 carbon atoms in the alkyl moiety; imidazolylcarbonyl; alkylimidazolylcarbonyl of 1 to 4 carbon atoms in the alkyl moiety; thiazolylcarbonyl; nitrothiazolylcarbonyl; oxazolylcarbonyl; isoxazolylcarbonyl; alkylisoxazolylcarbonyl of 1 to 4 carbon atoms in the alkyl moiety; halopicolinylcarbonyl; nicotinylcarbonyl; halonicotinylcarbonyl; pyridazinylcarbonyl; pyrimidinylcarbonyl; pyrazinylcarbonyl; alkylpiperazinylcarbonyl of 1 to 4 carbon atoms in the alkyl moiety; dihydrofurylcarbonyl; tetrahydrofurylcarbonyl; tetrahydropyridylcarbonyl; alkylpiperadylcarbonyl of 1 to 4 carbon atoms in the alkyl moiety; tetrahydropyranylcarbonyl; tetrahydrothiopyranylcarbonyl; thiadiazolylcarbonyl; morpholinocarbonyl; or phenylsulphonyl substituted by 1 or 2 substituents selected from the group consisting of alkyl of 1 to 4 carbon atoms, halo and nitro, or by 1 trifluoromethylsulphonyl moiety;

X is methylene; ethylene; oxyethylene; oxyethylene wherein 1 hydrogen atom on 1 of the carbon atoms is substituted by alkyl of 1 to 4 carbon atoms; or thioethylene; and $R^2$ is phenyl unsubstituted or substituted by 1 or 2 substituents selected from the group consisting of alkyl of 1 to 4 carbon atoms, halo, and trifluoromethyl; tetramethylenephenyl; naphthyl; or pyridyl.

According to another embodiment of the present invention

R is methyl; ethyl; propyl; trifluoromethyl or phenyl;

$R^1$ is hydrogen; methyl; ethyl; phenyl; chlorophenyl or fluorophenyl;

$R^3$ is acetyl; propionyl; butyryl; trimethylacetyl; isovaleryl; ethoxycarbonyl and trifluoromethylcarbonyl; chloromethylcarbonyl; trichloromethylcarbonyl; chlorobutyryl; methoxymethylcarbonyl; ethoxymethylcarbonyl; benzoyl nuclear substituted by methyl, dimethyl, chloro, dichloro, fluoro, difluoro, ditrifluorofluoromethylsulphonyl; dimethylaminomethylcarbonyl; pyrrylcarbonyl; thienylcarbonyl; fluorothienylcarbonyl; furylcarbonyl; fluorofurylcarbonyl; pyrazolylcarbonyl; methylpyrazolylcarbonyl; imidazolylcarbonyl; methylimidazolylcarbonyl; thiazolylcarbonyl; nitrothiazolylcarbonyl; oxazolylcarbonyl; isoxazolylcarbonyl; methylisoxazolylcarbonyl; fluoropicolinylcarbonyl; nicotinylcarbonyl; fluoronicotinylcarbonyl; pyridazinylcarbonyl; pyrimidinylcarbonyl; pyrazinylcarbonyl; methylpiperazinylcarbonyl; dihydrofurycarbonyl; tetrahydrofurylcarbonyl; tetrahydropyridylcarbonyl; methylpiperidylcarbonyl; ethylpiperidylcarbonyl; tetrahydropyrranylcarbonyl; tetrahydrothiopyrranylcarbonyl; thiadiazolylcarbonyl; morpholinocarbonyl; fluorophenylsulphonyl; chlorophenylsulphonyl; methylphenylsulphonyl; dimethylphenylsulphonyl; nitrophenylsulphonyl; dinitrophenylsulphonyl; or trifluoromethylsulphonylmethylsulphonyl;

X is methylene; ethylene; oxyethylene, oxyethylene wherein 1 hydrogen atom on 1 of the carbon atoms is substituted by methyl, ethyl or propyl; or thioethylene; and $R^2$ is phenyl; phenyl substituted by methyl, dimethyl, chloro, dichloro, chloro and methyl fluoro, difluoro, trifluoromethyl, or ditrifluoromethyl; tetramethylenephenyl; naphthyl; or pyridyl.

According to another embodiment of the present invention

R is alkyl of 1 or 2 carbon atoms or benzyl;

$R^1$ is hydrogen or phenyl;

$R^3$ is alkylcarbonyl of 1 or 2 carbon atoms; ethoxycarbonyl of 1 or 2 carbon atoms; benzoyl nuclear substituted by alkyl of 1 or 2 carbon atoms, 1 or 2 halo atoms or alkoxy of 1 or 2 carbon atoms; phenoxyalkylcarbonyl of 1 to 4 carbon atoms in the alkyl moiety; furylcarbonyl; alkylsulphonyl of 1 or 2 carbon atoms in the alkyl moiety; or phenylsulphonyl unsubstituted or substituted by alkyl of 1 or 2 carbon atoms or by 1 or 2 halo atoms;

X is methylene or oxyethylene; and $R^2$ is phenyl; chlorophenyl; or naphthyl.

According to another embodiment of the present invention

R is methyl or benzyl;

$R^1$ is hydrogen or phenyl;

$R^3$ is acetyl; ethoxycarbonyl; benzoyl nuclear substituted by methyl, methoxy, chloro, dichloro, fluoro or nitro; phenoxyethylacetyl; furylcarbonyl; methylsulphonyl; phenylsulphonyl; methylphenylsulphonyl; chlorophenylsulphonyl; or dichlorophenylsulphonyl.

Depending on the nature of the starting materials used, the synthesis of the compounds according to the present invention can be represented by the following equation in which 3-phenyl-4-methyl-5-acetoxy-1-(3,4-dichlorobenzyl)-5-pyrazolone and acetyl chloride have been chosen as examples:

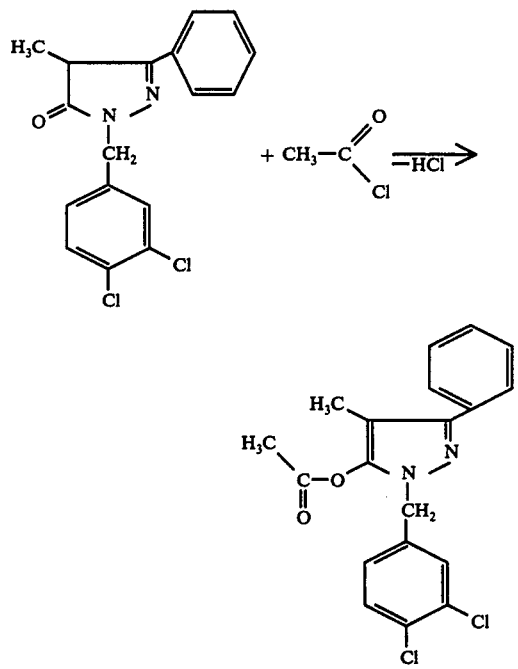

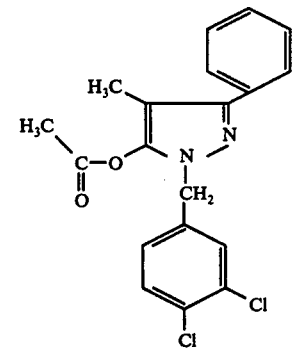

The 5-pyrazolone derivatives, of the formula II, used as starting materials, are known in some cases, or can be prepared in accordance with methods known from the literature (compare, for example, L. Knorr, Ber. dtsch. Chem. Ges. 16, 2,597 (1883)), by reacting hydrazines of the formula V with β-carbonyl-fatty acid derivatives of the formula VI:

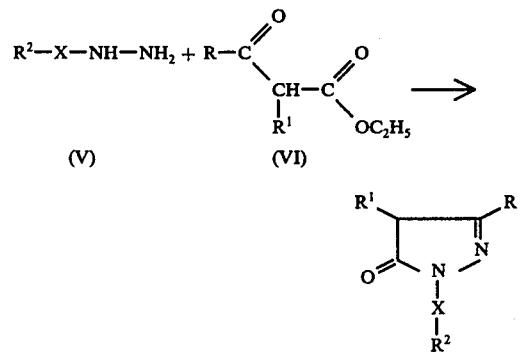

wherein R, $R^1$, $R^2$ and X are as above defined.

The following compounds are representative of the 5-pyrazolones of formula (II): 1-benzyl-5-pyrazolone, 1-(3,4-dichlorobenzyl)-5-pyrazolone, 1-(β-phenoxyethyl)-5-pyrazolone, 1-[β-(3-methylphenylmercapto)-ethyl]-5-pyrazolone, 1-(β-phenylethyl)-5-pyrazolone, 3-ethyl-1-(3-methyl-4-chlorobenzyl)-5-pyrazolone, 3-ethyl-1-(3-chloro-4-methylbenzyl)-5-pyrazolone, 3-ethyl-1-(3,4-dichlorobenzyl)-5-pyrazolone, 3-ethyl-1-(4-trifluoromethoxybenzyl)-5-pyrazolone, 3-ethyl-1-(4-methyl-3-trifluoromethylbenzyl)-5-pyrazolone, 3-ethyl-1-(4-bromo-3-chlorobenzyl)-5-pyrazolone, 3-ethyl-1-(α,β-dimethyl-β-phenylethyl)-5-pyrazolone, 4-methyl-1-(4-chlorobenzyl)-5-pyrazolone, 4-methyl-1-(4-methyl-3-chlorobenzyl)-5-pyrazolone, 3-methyl-1-[β-(4-iodophenoxy)-ethyl]-5-pyrazolone, 3-methyl-1-[β-(3,4-dichlorophenoxy)-ethyl]-5-pyrazolone, 3-methyl-1-[β-(3-chloro-4-methylphenoxy)-ethyl]-5-pyrazolone, 3-methyl-1-[β-(naphthyl-(2)-mercapto)-ethyl]-5-pyrazolone, 3-methyl-1-[β-methyl-β-(3-chlorophenylmercapto)-ethyl]-5-pyrazolone, 3-methyl-1-[β-methyl-β-(4-chlorophenylmercapto)-ethyl]-5-pyrazolone, 3-methyl-1-[β-methyl-β-(3,4-dichlorophenylmercapto)-ethyl]-5-pyrazolone, 3-methyl-1-(β-methyl-β-phenoxyethyl)-5-pyrazolone, 3-methyl-1-(β-ethyl-β-phenoxyethyl)-5-pyrazolone, 3-methyl-1-[β-methyl-β-(3-chlorophenoxy)-ethyl]-5-pyrazolone, 3-methyl-1-[β-methyl-β-(4-chlorophenoxy)-ethyl]-5-pyrazolone, 3-methyl-1-[β-n-propyl-β-(3,4-dichlorophenoxy-ethyl]-5-pyrazolone, 3-methyl-1-[β-(4-trifluoromethoxyphenoxy)-ethyl]-5-pyrazolone, 3-methyl-1-[β-(4-dimethylaminophenoxy)-ethyl]-5-pyrazolone, 3-ethyl-1-(β-phenylmercaptoethyl)-5-pyrazolone, 3-ethyl-1-[β-ethyl-β-(4-phenylphenoxy)-ethyl]-5-pyrazolone, 3-n-propyl-1-(β-phenoxyethyl)-5-pyrazolone, 3-n-butyl-1-(β-phenoxyethyl)-5-pyrazolone, 3-isopropyl-1-(3,4-dichlorobenzyl-5-pyrazolone, 3,4-dimethyl-1-(4-chlorobenzyl)-5-pyrazolone, 3,4-dimethyl-1-(4-bromobenzyl)-5-pyrazolone, 3,4-dimethyl-1-(3,4-dichlorobenzyl)-5-pyrazolone, 3,4-dimethyl-1-(4-bromo-3-chlorobenzyl)-5-pyrazolone, 3,4-dimethyl-1-(4-chloro-3-bromobenzyl)-5-pyrazolone, 3,4-dimethyl-1-(4-methylbenzyl)-5-pyrazolone, 3,4-dimethyl-1-(4-trifluoromethylbenzyl)-5-pyrazolone, 3,4-dimethyl-1-(4-methyl-3-chlorobenzyl)-5-pyrazolone, 3,4-dimethyl-1-(3-methyl-4-chlorobenzyl)-5-pyrazolone, 3,4-dimethyl-1-(4-trifluoromethyl-3-chlorobenzyl)-5-pyrazolone, 3,4-dimethyl-1-(4-methyl-3-trifluoromethylbenzyl)-5-pyrazolone, 3,4-dimethyl-1-(4-chloro-3-trifluoromethylbenzyl)-5-pyrazolone, 3,4-dimethyl-1-(naphthyl-(2)-methyl)-5-pyrazolone, 3,4-dimethyl-1-[β-(naphthyl)-(2)-ethyl]-5-pyrazolone, 3,4-dimethyl-1-(α,β-dimethyl-β-phenylethyl)-5-pyrazolone, 3,4-dimethyl-1-(β-methyl-β-phenoxyethyl)-5-pyrazolone, 3,4-dimethyl-1-[β-(naphthyl-(2)-oxy)-ethyl]-5-pyrazolone, 3-methyl-4-phenyl-1-(4-butylbenzyl)-5-pyrazolone, 3-methyl-4-phenyl-1-(3-trifluoromethyl-4-chlorobenzyl)-5-pyrazolone, 3-methyl-4-phenyl-1-(3,4-tetramethylenebenzyl)-5-pyrazolone, 3-methyl-4-phenyl-1-(3-chlorobenzyl)-5-pyrazolone, 3-methyl-4-phenyl-1-(4-fluorobenzyl)-5-pyrazolone, 3-methyl-4-phenyl-1-(4-fluoro-3-chlorobenzyl)-5-pyrazolone, 3-phenyl-1-(3-chlorobenzyl)-5-pyrazolone, 3-phenyl-1-(3-bromobenzyl)-5-pyrazolone, 3-phenyl-1-(3-fluorobenzyl)-5-pyrazolone, 3-phenyl-1-(4-fluorobenzyl)-5-pyrazolone, 3-phenyl-1-(4-iodobenzyl)-5-pyrazolone, 3-phenyl-1-(4-trifluoromethylbenzyl)-5-pyrazolone, 3-phenyl-1-(4-trifluoromethoxybenzyl)-5-pyrazolone, 3-phenyl-1-(3-trifluoromethyl-4-methylbenzyl)-5-pyrazolone, 3,4-diphenyl-1-(4-nitrobenzyl)-5-pyrazolone, 3,4-diphenyl-1-(4-cyanobenzyl)-5-pyrazolone, 3,4-diphenyl-1-(2-chloro-4-fluorobenzyl)-5-pyrazolone, 3,4-diphenyl-1-[β-(2-methylphenoxy)-ethyl]-5-pyrazolone, 3,4-diphenyl-1-[β-(2-chlorophenoxy)-ethyl]-5-pyrazolone, 3,4-diphenyl-1-(α-methyl-β-phenoxyethyl)-5-pyrazolone, 3,4-diphenyl-1-[α-methyl-β-(3-chloro-4-methylphenoxy)-ethyl]-5-pyrazolone, 3,4-diphenyl-1-[β-methyl-β-(4-cyclohexylphenoxy)-ethyl]-5-pyrazolone, 3,4-diphenyl-1-[β-(2-nitrophenoxy)-ethyl]-5-pyrazolone, 3,4-diphenyl-1-[β-ethyl-β-(4-isopropylphenoxy)-ethyl]-5-pyrazolone, 3,4-diphenyl-1-[β-(naphthyl-(2)-oxy)-ethyl]-5-pyrazolone, 3,4-diphenyl-1-[β-methyl-β-(4-methylphenylmercapto]-ethyl-5-pyrazolone, 3,4-diphenyl-1-[β-(naphthyl-(2)-mercapto)-ethyl]-5-pyrazolone, 3,4-diphenyl-1-[β-(3,4-trimethylenephenyl)-ethyl]-5-pyrazolone, 3,4-diphenyl-1-[β-(4-chlorophenyl)-ethyl]-5-pyrazolone, 3,4-diphenyl-1-[α,β-dimethyl-β-phenylethyl]-5-pyrazolone, 3,4-diphenyl-1-[β-methyl-β-(3-chloro-4-methylphenyl)-ethyl]-5-pyrazolone, 3,4-diphenyl-1-(α-ethyl-β-phenylethyl)-5-pyrazolone, 3-(4-chlorophenyl)-4-phenyl-1-(3-chlorobenzyl)-5-pyrazolone, 3-(3,4-dichlorophenyl)-4-phenyl-1-(β-phenoxyethyl)-5-pyrazolone, 3-methyl-4-phenyl-1-(pyridyl-(4)-methyl)-5-pyrazolone, 3,4-dimethyl-1-(pyridyl-(3)-methyl)-5-pyrazolone, 3-trifluoromethyl-1-(pyridyl-(4)-methyl)-5-pyrazolone, 3-trifluoromethyl-4-methyl-1-(β-naphthyl-(2)-ethyl)-5-pyrazolone, 3-trifluoromethyl-4-methyl-1-(3-chloro-4-methylbenzyl)-5-pyrazolone, 3-trifluoromethyl-4-phenyl-1-(3,4-tetramethylenebenzyl)-5-pyrazolone and 3-trifluoromethyl-4-methyl-1-(3,4-tetramethylenebenzyl)-5-pyrazolone.

In formula (III)

(III)

Y is preferably $R^6$ according to the embodiments set forth above.

A preferably is halo, such as fluoro, chloro or bromo, especially chloro, or a 5-membered heterocyclic azole ring, such as imidazole, pyrazole, 1,3,4-triazole, especially imidazole, wherein the heterocyclic ring is bonded to the carbonyl carbon atom in formula (III) via a nitrogen, or is $R^5$ which is bonded to the carbonyl atom in formula (III) via an oxygen atom or a sulphur atom and which is a straight or branched chain alkyl moiety of 1 to 4 carbon atoms, phenyl unsubstituted or substituted by 1 or 2 nitro moieties or an acyloxy moiety of the formula

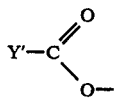

wherein Y' has the same meaning as Y but need not be identical to Y so that mixed anhydrides may also be employed.

The starting materials used in accordance with formula III are known from the literature and can be prepared according to methods known from the literature (compare, for example, Houben Weyl, Methoden der organischen Chemie (Methods of Organic Chemistry), VIII, page 101 (1952), Weygand/Hilgetag, Org. Chemische Experimentierkunst (The Art of Experimentation in Organic Chemistry), page 246, 4th edition, 1970, Verlag J. A. Barth, Leipzig).

The following compounds are representative of compounds (III): acetyl chloride, propionyl chloride, isopropionyl chloride, acetic anhydride, trifluoroacetic anhydride, propionic anhydride, butyric anhydride, β-methoxy-propionic acid chloride, phenylacetic acid chloride, phenoxyacetic acid chloride, 4-chlorophenoxyacetic acid chloride, ethoxycarbonyl acetate, phenoxycarbonyl acetate, benzoyl chloride, benzoic anhydride, thiobenzoic acid S-phenyl ester, ethoxycarbonyl benzoate, $N^1$-benzoylimidazolide, 4-chlorobenzoyl chloride, 4-fluorobenzoyl chloride, 4-trifluoromethylbenzoyl chloride, 4-trifluoromethylsulphonylbenzoyl chloride, 4-trifluoromethoxybenzoyl chloride, (4-trifluoromethylthio)-benzoyl chloride, 3,4-dichlorobenzoyl chloride, 3-chloro-4-methylbenzoyl chloride, 4-nitrobenzoyl chloride, 4-methoxybenzoyl chloride, chlorocarbonic acid ethyl ester, chlorocarbonic acid isobutyl ester, chlorocarbonic acid benzyl ester, chlorocarbonic acid β-methoxyethyl ester, chlorocarbonic acid β-phenoxyethyl ester, carbonic acid diethyl ester, carbonic acid di-n-butyl ester, pyrocarbonic acid diethyl ester, N,N-dimethylcarbamic acid chloride, N,N-diethylcarbamic acid chloride, N,N-di-n-butylcarbamic acid chloride, pyridine-2-carboxylic acid chloride, nicotinic acid chloride, isonicotinic acid chloride, thiophene-2-carboxylic acid chloride, thiophene-3-carboxylic acid chloride, furane-2-carboxylic acid chloride, furane-3-carboxylic acid chloride, pyrazole-4-carboxylic acid 4-nitrophenyl ester, the anhydride of pyrazole-3-carboxylic acid and carbonic acid monoethyl ester, 4-methyl-imidazole-5-carboxylic acid chloride, $N^1$-methyl-imidazole-4-carboxylic acid chloride, isoxazole-3-carboxylic acid chloride, 5-methyl-isoxazole-3-carboxylic acid chloride, isoxazole acid chloride, 5-methyl-isoxazole-4-carboxylic acid chloride, isoxazole-5-carboxylic acid chloride, 3-methyl-isoxazole-5-carboxylic acid chloride, isothiazole-3-carboxylic acid chloride, N-methylpyrrolidine-4-carboxylic acid chloride, ethoxycarbonyl-pyrrolidine-2-carboxylate, N-chlorocarbonyl-piperidine, N-methyl-N'-chlorocarbonyl-piperazine and N-chlorocarbonylmorpholine.

In formula (IV)

$$Z-SO_2-A' \qquad (IV)$$

Z is $R^7$ according to the embodiments set forth above and A' is halo.

The starting materials used according to formula IV are known from the literature or can be prepared according to methods known from the literature (compare, for example, Weygand/Hilgetag, *Org. Chemische Experimentierkunst* (The Art of Experimentation in Organic Chemistry), pages 69, 704 and 645, 4th edition, 1970, Verlag J. A. Barth, Leipzig).

The following may be mentioned as examples: methanesulphonic acid chloride, ethanesulphonic acid chloride, butanesulphonic acid chloride, benzenesulphonic acid chloride, p-toluenesulphonic acid chloride, 4-chlorobenzenesulphonic acid chloride, 3-chlorobenzenesulphonic acid chloride, 4-fluorobenzenesulphonic acid chloride, 3,4-dichlorobenzenesulphonic acid chloride and 3-chloro-4-methylbenzenesulphonic acid chloride.

Suitable diluents are all inert solvents. These preferentially include hydrocarbons such as benzene, toluene and xylene, halogenohydrocarbons, such as methylene chloride, chloroform, carbon tetrachloride and chlorobenzene, ethers, such as tetrahydrofurane, dioxane and glycol dimethyl ether, amides, such as dimethylformamide, N-methylpyrrolidone and dimethylacetamide, N-methylpyrrolidone and hexamethylphosphoric acid triamide, sulphoxides, such as dimethylsulphoxide, sulphones, such as sulpholane, and bases, such as pyridine, picoline, collidine, lutidine and quinoline.

Suitable basic auxiliaries are inorganic and organic bases. These preferentially include alkali metal hydroxides and alkali metal carbonates, such as sodium hydroxide or potassium carbonate, and tert.-amines, such as triethylamine or pyridine.

The reaction temperatures can be varied within a wide range. In general, the reaction is carried out at between −10° and 150° C, preferably between 0 and 100° C. It is carried out under normal pressure, but can also be carried out under a higher pressure in closed vessels.

In carrying out the process according to the invention, 1 mol of the 5-pyrazolone derivative is reacted with 1 to 5 mols of the carboxylic acid derivative, carbonic acid derivative or sulphonic acid derivative in an inert diluent, if appropriate in the presence of molar amounts of a basic auxiliary, such as triethylamine or pyridine. The compounds according to the invention, which in most cases are obtained in a crystalline form after removing the diluent, can easily be prepared in a pure form by recrystallization from a suitable solvent.

The following compounds, in addition to the examples set forth below, are representative of the compounds of the present invention: 5-acetoxy-3-methyl-1-(β-(3-chlorophenoxy)-ethyl)-pyrazole, 5-acetoxy-3-ethyl-1-(β-(3-methylphenoxy)-ethyl)-pyrazole, 5-acetoxy-3,4-dimethyl-1-(β-(3,4-dichlorophenoxy)-ethyl)-pyrazole, 5-acetoxy-3,4-dimethyl-1-(β-(3,5-dimethylphenoxy)-ethyl)-pyrazole, 5-acetoxy-3-ethyl-4-methyl-1-(β-(3-chloro-4-methylphenoxy)-ethyl)-pyrazole, 5-acetoxy-3,4-dimethyl-1-(α-methyl-β-(3-chlorophenoxy)-ethyl)-pyrazole, 5-acetoxy-3,4-dimethyl-1-(β-methyl-β-phenoxyethyl)-pyrazole, 5-acetoxy-3,4-dimethyl-1-(α-propyl-β-phenoxyethyl)-pyrazole, 5-acetoxy-3,4-dimethyl-1-(β-phenoxyethyl)-pyrazole, 5-acetoxy-3-methyl-4-ethyl-1-(β-phenoxyethyl)-pyrazole, 5-acetoxy-3-ethyl-4-methyl-1-(β-phenoxyethyl)-pyrazole, 5-acetoxy-3,4-diphenyl-1-(β-phenoxyethyl)-pyrazole, 5-acetoxy-3,4-dimethyl-1-(β-phenylthioethyl)-pyrazole, 5-acetoxy-3,4-dimethyl-1-(β-phenylethyl)-pyrazole, 5-acetoxy-3-methyl-4-phenyl-1-(β-(3-chlorophenyl)-ethyl)-pyrazole, 5-acetoxy-3-phenyl-4-methyl-1-(β-(3,4-dichlorophenyl)-ethyl)-pyrazole, 5-acetoxy-3,4-dimethyl-1-(3,4-tetramethylenebenzoyl)-pyrazole, 5-acetoxy-3-methyl-4-phenyl-1-(3,4-tetramethylenebenzyl)-pyrazole, 5-acetoxy-3,4-diphenyl-1-(3,4-tetramethylenebenzyl)-pyrazole, 5-acetoxy-3,4-dimethyl-1-(naphthyl-(2)-methyl)-pyrazole, 5-acetoxy-3-phenyl-4-methyl-1-(naphthyl-(2)-methyl)-pyrazole, 5-(4-trifluoromethylsulphonylphenylsulphonyloxy)-3-methyl-1-(β-(naphthyl-(2))-ethyl)-pyrazole, 5-(ethoxy-carbonyloxy)-3-methyl-1-(pyridyl-(3)-ethyl)-pyrazole, 5-acetoxy-3,4-dimethyl-1-(3,4-dichlorobenzyl)-pyrazole, 5-acetoxy-3-methyl-1-(β-(naphthyl-(2))-ethyl)-pyrazole, 5-acetoxy-4-methyl-1-(3,4-dichlorobenzyl)-pyrazole, 5-acetoxy-3-methyl-1-(4-fluorobenzyl)-pyrazole, 5-acetoxy-3,4-dimethyl-1-(β-(pyridyl-(3))-ethyl)-pyrazole, 5-acetoxy-3,4-dimethyl-1-(3,4-ditrifluoromethylbenzyl)-pyrazole, 5-propionyloxy-3-methyl-1-(3,4-dichlorobenzyl)-pyrazole, 5-propionyloxy-3,4-dimethyl-1-(3-chloro-4-methylbenzyl)-pyrazole, 5-propionyloxy-3-isopropyl-1-(3,4-dichlorobenzyl)-pyrazole, 5-n-butyryloxy-3-methyl-1-(3,4-dichlorobenzyl)-pyrazole, 5-trimethylacetoxy-3-methyl-1-(3-chloro-4-methylbenzyl)-pyrazole, 5-isovaleryloxy-3-methyl-1-(3,4-difluorobenzyl)-pyrazole, 5-trifluoroacetoxy-3-methyl-1-(3,4-dichlorobenzyl)-pyrazole, 5-trifluoroacetoxy-3,4-dimethyl-1-(3,4-dichlorobenzyl)-pyrazole, 5-trifluoroacetoxy-3-methyl-1-(3-chloro-4-methylbenzyl)-pyrazole, 5-trifluoroacetoxy-3,4-dimethyl-1-(3-chloro-4-methylbenzyl)-pyrazole, 5-trifluoroacetoxy-3-methyl-1-(fluorobenzyl)-pyrazole, 5-trifluoroacetoxy-3-methyl-1-(4-trifluoromethylbenzyl)-pyrazole, 5-trifluoroacetoxy-3,4-dimethyl-1-(3,4-ditrifluoromethylbenzyl)-pyrazole, 5-chloroacetoxy-3-methyl-1-(3,4-dichlorobenzyl)-pyrazole, 5-chloroacetoxy-3-methyl-1-(3-chloro-4-methylbenzyl)-pyrazole, 5-chloroacetoxy-3-methyl-1-(4-chloro-3-methylbenzyl)-pyrazole, 5-dichloroacetoxy-3-methyl-1-(3,4-dichlorobenzyl)-pyrazole, 5-dichloroacetoxy-3-methyl-1-(3-chloro-4-methylbenzyl)-pyrazole, 5-dichloroacetoxy-3,4-dimethyl-1-(3,4-dichlorobenzyl)-pyrazole, 5-trichloroacetoxy-3-methyl-1-(3,4-dichlorobenzyl)-pyrazole, 5-(3-chloropropionyloxy)-3-methyl-1-(3,4-dichlorobenzyl)-pyrazole, 5-(2-methoxyacetoxy)-3-methyl-1-(3,4-dichlorobenzyl)-pyrazole, 5-(2-methoxyacetoxy)-3-methyl-1-(3-chloro-4-methylbenzyl)-pyrazole, 5-(2-ethoxyacetoxy)-3-methyl-1-(3,4-dichlorobenzyl)-pyrazole, 5-(2-dimethylaminoacetoxy)-3-methyl-1-(3-chloro-4-methylbenzyl)-pyrazole, 5-(2-fluorobenzoyloxy)-3,4-dimethyl-1-(3,4-dichlorobenzyl)-pyrazole, 5-(3-fluorobenzoyloxy)-3-methyl-1-(3,4-difluorobenzyl)-pyrazole, 5-(4-fluorobenzoyloxy)-3-methyl-1-(4-fluorobenzyl)-pyrazole, 5-(4-nitrobenzoyloxy)-3-methyl-1-(4-chlorobenzyl)-pyrazole, 5-(4-nitrobenzoyloxy)-3-methyl-1-(3,4-dichlorobenzyl)-pyrazole, 5-(3,4-dinitrobenzoyloxy)-3-methyl-1-(3-chloro-4-methylbenzyl)-pyrazole, 5-(3-methylbenzoyloxy)-3-methyl-1-(3-chlorobenzyl)-pyrazole, 5-(3,4-dimethylbenzoyloxy)-3-methyl-1-(3,4-dichlorobenzyl)-pyrazole, 5-(3-chlorobenzoyloxy)-3-methyl-1-(3-trifluoromethylbenzyl)-pyrazole, 5-(3,4-dichlorobenzoyloxy)-3,4-dimethyl-1-(3,4-dimethylbenzyl)-pyrazole, 5-(3,5-difluorobenzoyloxy)-3-methyl-1-(3,4-dichlorobenzyl)-pyrazole, 5-(3,5-dinitrobenzoyloxy)-3-methyl-1-(3-methyl-4-chlorobenzyl)-pyrazole, 5-(3,4-ditrifluoromethylbenzoyloxy)-3-methyl-1-(3,4-dichlorobenzyl)-pyrazole, 5-(4-trifluoromethylsulphonylbenzoyloxy)-3-methyl-1-(naphthyl-(2)-methyl)-pyrazole, 5-(4-trifluoromethoxybenzoyloxy)-3-phenyl-1-(3,4-dichlorobenzyl)-pyrazole, 5-(pyrryl-(2)-carbonyloxy)-3,4-diphenyl-1-(3,4-dichlorobenzyl)-pyrazole, 5-(pyrryl-(3)-carbonyloxy)-3,4-dimethyl-1-(3-chloro-4-methylbenzyl)-pyrazole, 5-(thienyl-(2)-carbonyloxy)-3-methyl-1-(β-(pyridyl-(2))-ethyl)-pyrazole, 5-(thienyl-(2)-carbonyloxy)-3,4-dimethyl-1-(β-phenoxyethyl)-pyrazole, 5-(thienyl-(2)-carbonyloxy)-3-methyl-4-phenyl-1-(β-(3,4-dichlorophenoxy)-ethyl)-pyrazole, 5-(thienyl-(3)-carbonyloxy)-3,4-diphenyl-1-(β-(3,4-difluorophenoxy)-ethyl)-pyrazole, 5-(thienyl)-(3)-carbonyloxy)-3-trifluoromethyl-1-(3,4-difluorobenzyl)-pyrazole, 5-(3-fluorothienyl-(2)-carbonyloxy)-3-methyl-1-(β-naphthyl-(2)-ethyl-pyrazole, 5-(3-fluorothienyl-(2)-carbonyloxy)-3-methyl-1-(β-phenoxyethyl)-pyrazole, 5-(4-fluorothienyl-(2)-carbonyloxy)-3,4-dimethyl-1-(β-(3-chlorophenoxy)-ethyl)-pyrazole, 5-(5-fluorothienyl-(2)-carbonyloxy)-3-phenyl-1-(β-naphthyl-(2)-oxy-ethyl)-pyrazole, 5-(furyl-(2)-carbonyloxy)-3-methyl-1-(β-phenoxyethyl)-pyrazole, 5-(furyl-(3)-carbonyloxy)-3-methyl-1-(β-phenoxyethyl)-pyrazole, 5-(4-fluorofuryl-(2)-carbonyloxy)-3-methyl-1-(3,4-dichlorobenzyl)-pyrazole, 5-(pyrazolyl-(3)-carbonyloxy)-3-methyl-1-(β-phenoxyethyl)-pyrazole, 5-(pyrazolyl-(4)-carbonyloxy)-3,4-dimethyl-1-(β-phenoxyethyl)-pyrazole, 5-(4-methylpyrazolyl-(3)-carbonyloxy)-3-phenyl-4-(4-chlorophenyl)-1-(β-phenoxyethyl)-pyrazole, 5-(4-methylpyrazolyl-(3)-carbonyloxy)-3-methyl-1-(β-pyridyl-(3)-ethyl)-pyrazole, 5-(5-methylpyrazolyl-(3)-carbonyloxy)-3-methyl-4-ethyl-1-(β-phenoxyethyl)-pyrazole, 5-(4-methylimidazolyl-(2)-carbonyloxy)-3-ethyl-1-(β-phenoxyethyl)-pyrazole, 5-(4-methylimidazolyl-(3)-carbonyloxy)-3,4-dimethyl-1-(β-(3-chlorophenoxy)-ethyl)-pyrazole, 5-(2-methylimidazolyl-(4)-carbonyloxy)-3-phenyl-4-methyl-1-(β-(3,4-difluorophenyl)-ethyl)-pyrazole, 5-(imidazolyl-(2)-carbonyloxy)-3,4-dimethyl-1-(β-phenoxyethyl)-pyrazole, 5-(imidazolyl-(2)-carbonyloxy)-4-methyl-1-(3,4-dichlorobenzyl)-pyrazole, 5-(imidazolyl-(4)-carbonyloxy)-4-ethyl-1-(β-phenoxyethyl)-pyrazole, 5-(thiazolyl-(2)-carbonyloxy)-3-methyl-4-ethyl-1-(β-(naphthyl-(2)-oxy-ethyl)-pyrazole, 5-(thiazolyl-(4)-carbonyloxy)-3,4-dimethyl-1-(β-(3,5-dichlorophenoxy)-ethyl)-pyrazole, 5-(thiazolyl-(5)-carbonyloxy)-3-methyl-1-(β-(pyridyl-(3)-ethyl)-pyrazole, 5-(5-nitrothiazolyl-(2)-carbonyloxy)-3-methyl-1-(β-naphthyl-(2))-ethyl)-pyrazole, 5-(oxazolyl-(2)-carbonyloxy)-3-methyl-1-(3,4-dichlorobenzyl)-pyrazole, 5-(oxazolyl-(4)-carbonyloxy)-3,4-dimethyl-1-(3,4-dichlorobenzyl)-pyrazole, 5-(oxazolyl-(4)-carbonyloxy)-3-methyl-1-(β-phenoxyethyl)-pyrazole, 5-(oxazolyl-(4)-carbonyloxy)-3,4-dimethyl-1-(α-methyl-β-phenoxyethyl)-pyrazole, 5-(oxazolyl-(5)-carbonyloxy)-3-methyl-1-(4-fluorobenzyl)-pyrazole, 5-(oxazolyl-(5)-carbonyloxy)-3,4-dimethyl-1-(β-(3-fluorophenoxy)-ethyl)-pyrazole, 5-(oxazolyl-(5)-carbonyloxy)-3-phenyl-1-(β-phenoxyethyl)-pyrazole, 5-(isoxazolyl-(3)-carbonyloxy)-3-methyl-1-(3,4-dichlorobenzyl)-pyrazole, 5-(isoxazolyl-(4)-carbonyloxy)-3,4-dimethyl-1-(4-chlorobenzyl)-pyrazole, 5-(isoxazolyl-(5)-carbonyloxy)-3-methyl-1-(3-chlorobenzyl)-pyrazole, 5-(isoxazolyl-(3)-carbonyloxy)-3-(4-chlorophenyl)-1-(β-(naphthyl-(2)-oxy)-ethyl)-pyrazole, 5-(isoxazolyl-(5)-carbonyloxy)-3,4-dimethyl-1-(α-methyl-β-(3-fluorophenoxy)-ethyl)-pyrazole, 5-(5-methylisoxazolyl-(3)-carbonyloxy)-3-methyl-4-phenyl-1-(β-(3,4-dichlorophenyl)-ethyl)-pyrazole, 5-(5-methylisoxazolyl-(3)-carbonyloxy)-3-methyl-4-phenyl-1-(β-(4-chlorophenyl)-ethyl)-pyrazole, 5-(4-methylisoxazolyl-(3)-carbonyloxy)-3-methyl-1-(β-phenoxyethyl)-pyrazole, 5-(3-fluoropicolinoyloxy)-3-methyl-1-(3,4-dichlorobenzyl)-pyrazole, 5-(4-fluoropicolinoyloxy)-3,4-dimethyl-1-(3,4-dichlorobenzyl)-pyrazole, 5-(5-fluoropicolinoyloxy)-3-methyl-1-(3,4-difluorobenzyl)-pyrazole, 5-(6-fluoropicolinoyloxy)-3-methyl-1-(3,4-dichlorobenzyl)-pyrazole, 5-(picolinoyloxy)-4-methyl-1-(3,4-dichlorobenzyl)-pyrazole, 5-(nicotinoyloxy)-3-methyl-4-(3,4-dichlorophenyl)-1-(β-phenoxyethyl)-pyrazole, 5-(2-fluoronicotinoyloxy)-3-methyl-1-(β-phenoxyethyl)-pyrazole, 5-(4-fluoronicotinoyloxy)-3,4-dimethyl-1-(β-phenoxyethyl)-pyrazole, 5-(pyridazinyl-(3)-carbonyloxy)-3-methyl-1-(β-phenoxyethyl)-pyrazole, 5-(pyridazinyl-(4)-carbonyloxy)-3-methyl-1-(β-phenoxyethyl)-pyrazole, 5-(pyrimidinyl-(2)-carbonyloxy)-3-methyl-1-(β-phenoxyethyl)-pyrazole, 5-(pyrimidinyl-(4)-carbonyloxy)-3-methyl-1-(β-phenoxyethyl)-pyrazole, 5-(pyrimidinyl-(5)-carbonyloxy)-3-methyl-1-(β-phenoxyethyl)-pyrazole, 5-(pyrazinyl-(2)-carbonyloxy)-3-methyl-1-(β-phenoxyethyl)-pyrazole, 5-(4-methyl-piperazinyl-(1)-carbonyloxy)-3-methyl-1-(β-phenoxyethyl)-pyrazole, 5-(dihydrofuryl-(2)-carbonyloxy)-3-methyl-4-phenyl-1-(β-phenoxyethyl)-pyrazole, 5-(tetrahydrofuryl-(2)-carbonyloxy)-3,4-dimethyl-1-(β-phenoxyethyl)-pyrazole, 5-(tetrahydrofuryl-(3)-carbonyloxy)-3-methyl-4-(4-chlorophenyl)-1-(β-phenoxyethyl)-pyrazole, 5-(1-methyl-1,4,5,6-tetrahydropyridyl-(3)-carbonyloxy)-3-phenyl-1-(β-phenoxyethyl)-pyrazole, 5-(1-methylpiperidyl-(2)-carbonyloxy)3-methyl-1-(β-phenoxyethyl)-pyrazole, 5-(1-methylpiperidyl-(3)-carbonyloxy)-3-methyl-4-phenyl-1-(β-phenoxyethyl)-pyrazole, 5-(1-methylpiperidyl-(4)-carbonyloxy)-3-methyl-4-(3-chlorophenyl)-1-(β- phenoxyethyl)-pyrazole, 5-(1-ethylpiperidyl-(2)-carbonyloxy)-3,4-dimethyl-1-(β-phenoxyethyl)-pyrazole, 5-(tetrahydropyranyl-(2)-carbonyloxy)-3-methyl-4-ethyl-1-(β-phenoxyethyl)-pyrazole, 5-(tetrahydrothiopyranyl-(2)-carbonyloxy)-3-methyl-4-phenyl-1-(β-phenoxyethyl)-pyrazole, 5-(tetrahydrothiopyranyl-(3)-carbonyloxy)-3-methyl-1-(β-phenoxyethyl)-pyrazole, 5-(tetrahydrothiopyranyl-(4)-carbonyloxy)-3-methyl-4-(3-fluorophenyl)-1-(β-phenoxyethyl)-pyrazole, 5-(1,2,3-thiadiazolyl-(4)-carbonyloxy)-3,4-dimethyl-(β-phenoxyethyl)-pyrazole, 5-(morpholinocarbonyloxy)-3-methyl-4-phenyl-(β-phenoxyethyl)-pyrazole, 5-(2-fluorophenylsulphonyloxy)-3,4-dimethyl-1-(β-phenoxyethyl)-pyrazole, 5-(4-fluorophenylsulphonyloxy)-3-methyl-1-(β-phenoxyethyl)-pyrazole, 5-(4-nitrophenylsulphonyloxy-3-methyl-4-phenyl-1-(β-phenoxyethyl)-pyrazole, 5-(3,4-dinitrophenylsulphonyloxy)-3-methyl-1-(β-phenoxyethyl)-pyrazole, 5-(3-methylphenylsulphonyloxy)-3-methyl-1-(3-chlorobenzyl)-pyrazole, 5-(3,4-dimethylphenylsulphonyloxy)-3-methyl-1-(β-(3,4-dichlorophenyl)-ethyl)-pyrazole and 5-(3-chlorophenylsulphonyloxy)-3-methyl-1-(β-(3,4-dichlorophenylthio)-ethyl)-pyrazole.

The pharmaceutical compositions of the present invention contain a major or minor amount e.g. 0.1 to 99.5%, preferably 0.5 to 90%, of active ingredient as above defined in combination with a pharmaceutically acceptable nontoxic inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgement and considering the age, weight and condition of the recipient, the route of administration and the nature and gravity of the illness, generally the dosage will be from 0.01 to 500 mg/kg of body weight per day. In some instances a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinylpyrrolidone, a solution retardant such as paraffin, a resorption accellerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polishcoating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administation. Non-toxic salts and salt solutions can be added to render the injection isotonic.

Rectal administration can be effected utilizing suppositories in which the compound is admixed with low-melting, water-soluble or insoluble solids such as polyethylene glycol, cocoa butter, higher esters as for example myristyl palmitate, or mixtures thereof.

While routes of administration include oral, parenteral (i.e., intramuscular, intraperitoneal and intravenous) and rectal, oral and parenteral administration are particularly preferred.

The preferred daily dose, in the case of parenteral administration, is 0.01 to 50 mg/kg, preferably 0.1 to 10 mg/kg of body weight daily; while for oral administration the preferred daily dose is about 0.1 to 500 mg/kg, preferably 0.5 to 100 mg/kg, of body weight daily.

The preferred pharmaceutical compositions are therefore those in a form suitable for oral administration, such as tablets and suspensions, and those suitable for parenteral application, such as solutions and suspensions, to effect diuresis, saluresis and to treat hypertension by eliminating water and salts and also are useful for the treatment of prophylaxis of thromboembolic diseases. In addition, the compounds are useful for the treatment of oedemacious and hypertonic conditions and for flooding out of toxic substances so that they may be used in the case of acute kidney failure.

The following formulation is given by way of example: 200 g of 5-(p-chlorobenzoyloxy)-3-methyl-4-phenyl-1-($\beta$-(3-methylphenoxy)-ethyl)-pyrazole are ground to a powder which is mixed with 300 g of lactose and 200 g of potato starch and, after moistening with an aqueous gelatine solution, the mixture is granulated by passing through a sieve. After drying, 60 g of talc and 5 g of sodium lauryl-sulphate are added. From this mixture about 10,000 tablets each containing 20 mg of active compound are pressed.

To demonstrate the antithrombotic action of the compounds according to the invention, 5-(furyl-(2)-carbonyloxy)-3-methyl-1-(2-($\beta$-naphthyloxy)-ethyl)-pyrazole, described in Example 20, was administered to rats.

The remaining compounds show comparable properties.

The left jugular vein of rats weighing 170 to 180 g was exposed under ether narcosis and supercooled to $-12°$ C for 2 minutes to stimulate thromb formation. The thromb was isolated from the vein 4 hours later, and was weighed. The test animals were given the test preparation in tragacanth mucilage immediately before supercooling the wall of the blood vessel. As a result, the protective antithrombotic activity was tested in the first 4 hours after stimulating thromb formation.

The results of the investigations using the compounds according to the invention are shown in the table which follows:

Table

|  | Control on animals without active compound | Animals treated with the compound according to the invention (10 mg/kg, administered orally) |
|---|---|---|
| Thromb size in $\mu$g, mean value | 115 $\pm$ 12 | 45 $\pm$ 10 |
| Number of experiments | 14 | 12 |
| Inhibition in % | 0 | 61 |

The results show that the compounds according to the invention significantly inhibit the formation of venous thrombs.

After a 4 hour period of action, the size of the thrombs has been reduced by 61%.

The compounds according to the invention can therefore be used for the prophylaxis of thrombolic diseases.

In addition to the inhibiting action on the formation of thrombs, the compounds according to the invention are also distinguished by a very powerful thrombolytic action. Thrombotic deposits already formed are redispersed under the influence of the compound. Corresponding thrombolytic effects were hitherto only achievable by repeated intravenous administration of toxic fibrinolytics such as streptokinase and urokinase, while the compounds according to the invention are administered orally and only once daily.

The following nonlimitative examples more particularly illustrate the present invention:

EXAMPLE 1

5-(4-Chlorobenzoyloxy)-3-methyl-4-phenyl-1-(4-chlorobenzyl)-pyrazole

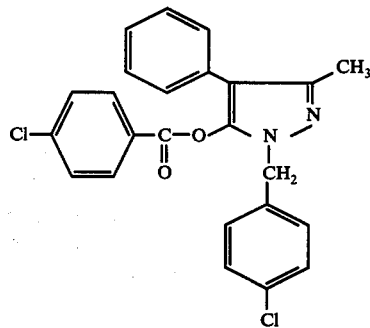

0.1 mol (29.9 g) of 3-methyl-4-phenyl-1-(p-chlorobenzyl)-5-pyrazolone were dissolved in 400 ml of absolute dioxane. After adding 15 ml of triethylamine, 0.11 mol (17.6 g) of 4-chlorobenzoyl chloride in dioxane was added dropwise. After heating for several hours under reflux, the reaction batch was worked up as follows:

The organic phase obtained after cooling, and after filtering off the precipitates of crystalline salt was concentrated, the residue was taken up in methylene chloride, and the methylene chloride solution was repeatedly extracted by shaking with water and was dried with sodium sulphate.

The crystalline crude product obtained after concentrating the methylene chloride phase was recrystallized from ethanol. Melting point: 125°–127° C.

Yield: 82% of theory.

EXAMPLE 2

5-(Ethoxycarbonyloxy)-3-methyl-1-($\beta$-phenoxyethyl)-pyrazole

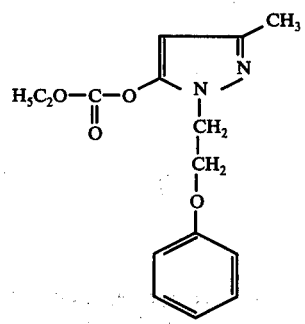

0.1 mol (21.8 g) of 3-methyl-1-($\beta$-phenoxyethyl)-5-pyrazolone was boiled with 10 mols of pyrocarbonic acid diethyl ester for 2 hours. The oily residue obtained after concentrating the reaction solution was distilled, using an oil pump. The oily distillated became crystalline on trituration with methanol. It was possible to recrystallize it from a little ether.

Melting point: 35°–36° C.
Yield: 52% of theory.

EXAMPLE 3

5-(Acetoxy)-3-methyl-1-(β-phenoxyethyl)-pyrazole

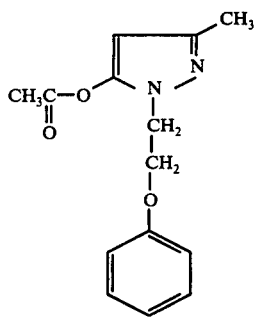

0.1 mol (21.8 g) of 3-methyl-1-(β-phenoxyethyl)-5-pyrazolone was heated with 0.2 mol (20.4 g) of acetic anhydride in the presence of 0.11 mol (8.2 g) of sodium acetate for 2 hours.

After cooling, the reaction mixture was poured onto ice/$H_2O$. The oily reaction product hereupon obtained was taken up in ether, the ether solution was dried with sodium sulphate and after stripping off the solvent on a rotary evaporator the product was distilled under an oil pump vacuum.

It was possible to cause the semi-solid distillate obtained to crystallize by treating it with methanol, and to recrystallize it from methanol.

Melting point: 84°–86° C.
Yield: 63% of theory.

EXAMPLE 4

5-(4-Chlorobenzoyloxy)-3-benzyl-1-(β-phenoxyethyl)-pyrazole

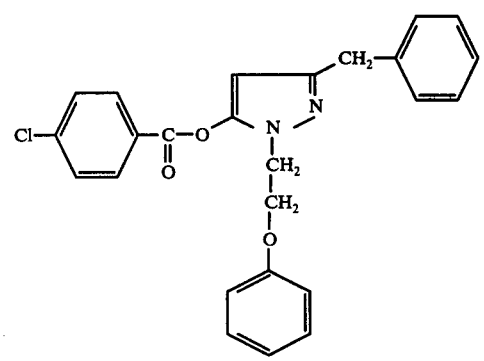

5-(4-Chlorobenzoyloxy)-3-benzyl-1-(β-phenoxyethyl)-pyrazole was obtained analogously to the procedure described in Example 1 from 3-benzyl-1-(β-phenoxyethyl)-5-pyrazolone and 4-benzoyl chloride.

Melting point: 121°–122° C (ethyl acetate).
Yield: 81% of theory.

EXAMPLE 5

5-(4-Methylbenzoyloxy)-3-benzyl-1-(β-phenoxyethyl)-pyrazole

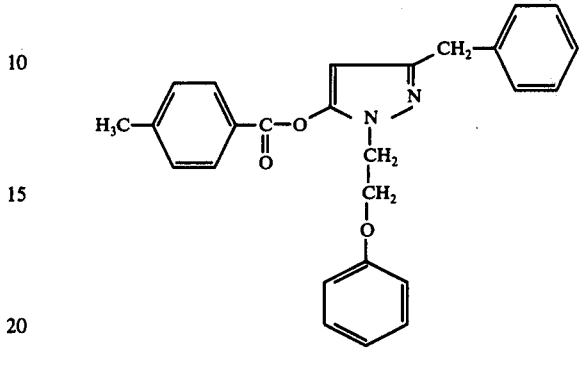

5-(4-Methylbenzoyloxy)-3-benzyl-1-(β-phenoxyethyl)-pyrazole was obtained analogously to the procedure described in Example 1 from 3-benzyl-1-(β-phenoxyethyl)-5-pyrazolone and 4-methylbenzoyl chloride.

Melting point: 110°–111° C (ethyl acetate).
Yield: 70% of theory.

EXAMPLE 6

5-(4-Chlorobenzoyloxy)-3-methyl-4-phenyl-1-(β-phenoxyethyl)-pyrazole

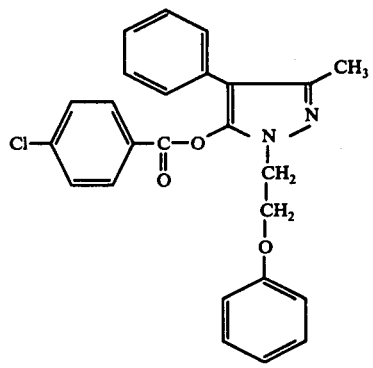

5-(4-Chlorobenzoyloxy)-3-methyl-4-phenyl-1-(β-phenoxyethyl)-pyrazole was obtained analogously to the procedure described in Preparation Example 1 from 3-methyl-4-phenyl-1-(β-phenoxyethyl)-5-pyrazolone and 4-benzoyl chloride.

Melting point: 131°–133° C (ethanol with a little DMF).
Yield: 88% of theory.

EXAMPLE 7

5-Acetoxy-3-methyl-1-(2-(β-naphthyloxy)-ethyl)-pyrazole

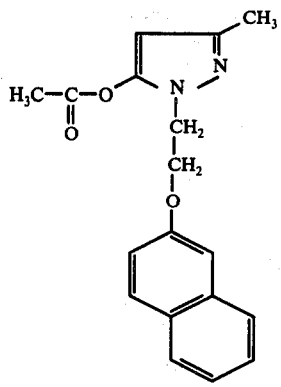

5-Acetoxy-3-methyl-1-(2-(β-naphthyloxy)-ethyl)-pyrazole was obtained analogously to the procedure described in Preparation Example 1 from 3-methyl-1-(2-(β-naphthyloxy)-ethyl)-5-pyrazolone and acetyl chloride.

Melting point: 87°–89° C (ethanol).
Yield: 62% of theory.

EXAMPLE 8

5-(3-Chlorobenzoyloxy-3-methyl)-1-(2-(β-naphthyloxy)-ethyl)-pyrazole

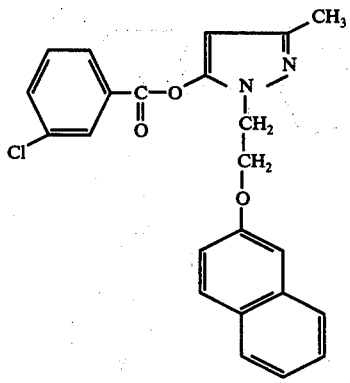

5-(3-Chlorobenzoyloxy)-3-methyl-1-(2-(β-naphthyloxy)-ethyl)-pyrazole was obtained analogously to the procedure described in Preparation Example 1 from 3-methyl-1-(2-(β-naphthyloxy)-ethyl)-5-pyrazolone and 3-chlorobenzoyl chloride.

Melting point: 110°–112° C (ethanol).
Yield: 80% of theory.

EXAMPLE 9

5-(2-Chlorobenzoyloxy)-3-methyl-1-(2-(β-naphthyloxy)-ethyl)-pyrazole

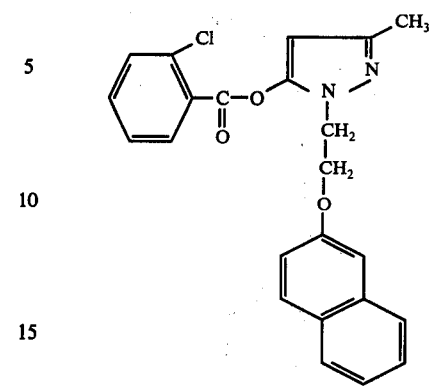

5-(2-Chlorobenzoyloxy)-3-methyl-1-(2-(β-naphthyloxy)-ethyl)-pyrazole was obtained analogously to Preparation Example 1 from 3-methyl-1-(2-(β-naphthyloxy)-ethyl)-5-pyrazolone and 2-chlorobenzoyl chloride.

Melting point: 102°–104° C (ethanol).
Yield: 78% of theory.

EXAMPLE 10

5-(4-Chlorobenzoyloxy)-3-methyl-1-(2-(β-naphthyloxy)-ethyl)-pyrazole

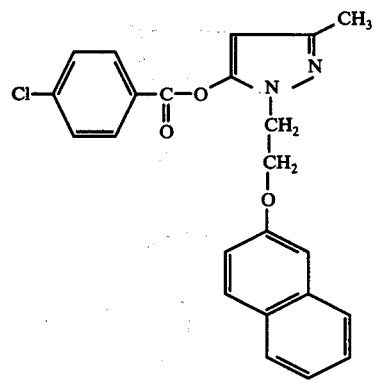

5-(4-Chlorobenzoyloxy)-3-methyl-1-(2-(β-naphthyloxy)-ethyl)-pyrazole was obtained analogously to the procedure described in Preparation Example 1 from 3-methyl-1-(2-(β-naphthyloxy)-ethyl)-5-pyrazolone and 4-chlorobenzoyl chloride.

Melting point: 142°–144° C (ethanol).
Yield: 93% of theory.

EXAMPLE 11

5-(4-Fluorobenzoyloxy)-3-methyl-1-(2-(β-naphthyloxy)-ethyl)-pyrazole

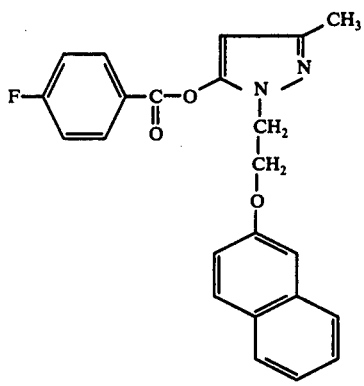

5-(4-Fluorobenzoyloxy)-3-methyl-1-(2-(β-naphthyloxy)-ethyl)-pyrazole was obtained analogously to the procedure described in Preparation Example 1 from 3-methyl-1-(2-(β-naphthyloxy)-ethyl)-5-pyrazolone and 4-fluorobenzoyl chloride.

Melting point: 126°–128° C.

Yield: 80% of theory.

EXAMPLE 12

5-(4-Methylbenzoyloxy)-3-methyl-1-(2-(β-naphthyloxy)-ethyl)-pyrazole

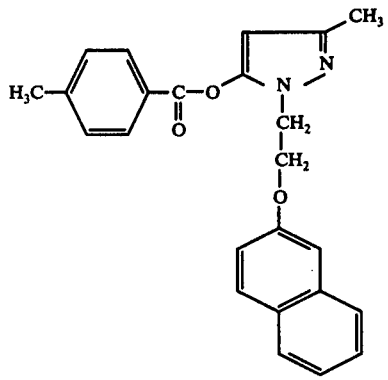

5-(4-Methylbenzoyloxy)-3-methyl-1-(2-(β-naphthyloxy)-ethyl)-pyrazole was obtained analogously to the procedure described in Preparation Example 1 from 3-methyl-1-(2-(β-naphthyloxy)-ethyl)-5-pyrazolone and 4-methylbenzoyl chloride.

Melting point: 132°–133° C (ethanol).

Yield: 79% of theory.

EXAMPLE 13

5-(2-Methoxybenzoyloxy)-3-methyl-1-(2-(β-naphthyloxy)-ethyl)-pyrazole

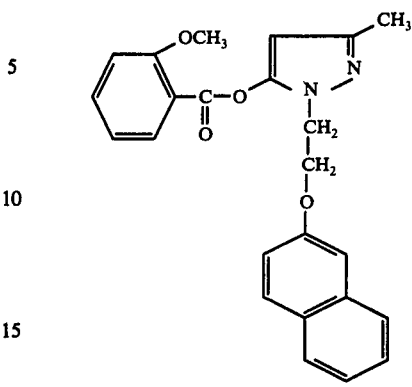

5-(2-Methoxybenzoyloxy)-3-methyl-1-(2-(β-naphthyloxy)-ethyl)-pyrazole was obtained analogously to the procedure described in Preparation Example 1 from 3-methyl-1-(2-(β-naphthyloxy)-ethyl)-5-pyrazolone and 2-methoxybenzoyl chloride.

Melting point: 102°–104° C (methanol).

Yield: 71% of theory.

EXAMPLE 14

5-(4-Methoxybenzoyloxy)-3-methyl-1-(2-(β-naphthyloxy)-ethyl)-pyrazole

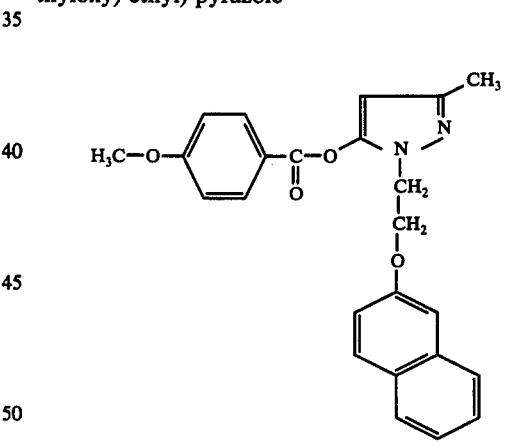

5-(4-Methoxybenzoyloxy)-3-methyl-1-(2-(β-naphthyloxy)-ethyl)-pyrazole was obtained analogously to the procedure described in Preparation Example 1 from 3-methyl-1-(2-(β-naphthyloxy)-ethyl)-5-pyrazolone and 4-methoxybenzoyl chloride.

Melting point: 119°–121° C (ethanol).

Yield: 80% of theory.

EXAMPLE 15

5-(4-Nitrobenzoyloxy)-3-methyl-1-(2-(naphthyloxy)-ethyl)-pyrazole

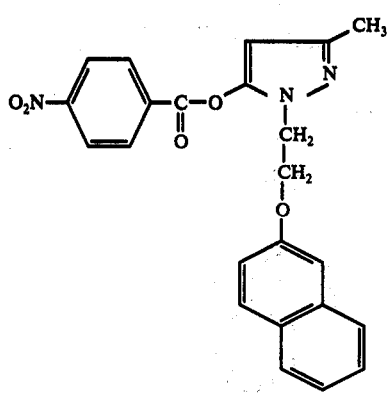

5-(4-Nitrobenzoyloxy)-3-methyl-1-(2-(naphthyloxy)-ethyl)-pyrazole was obtained analogously to the procedure described in Example 1 from 3-methyl-1-(2-(naphthyloxy)-ethyl)-5-pyrazolone and 4-nitrobenzoyl chloride.

Melting point: 137°–139° C (ethanol).

Yield: 72% of theory.

EXAMPLE 16

5-(2,5-Dichlorobenzoyloxy)-3-methyl-1-(2-(β-naphthyloxy)-ethyl)-pyrazole

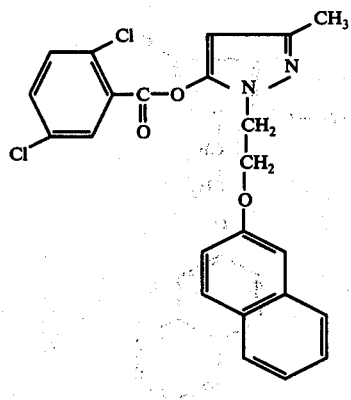

5-(2,5-Dichlorobenzoyloxy)-3-methyl-1-(2-(β-naphthyloxy)-ethyl)-pyrazole was obtained analogously to the procedure described in Example 1 from 3-methyl-1-(2-(β-naphthyloxy)-ethyl-5-pyrazolone and 2,5-dichlorobenzoyl chloride.

Melting point: 122°–124° C (ethanol with a little DMF).

Yield: 82% of theory.

EXAMPLE 17

5-Acetoxy-3-methyl-4-phenyl-1-(2-(β-naphthyloxy)-ethyl) pyrazole

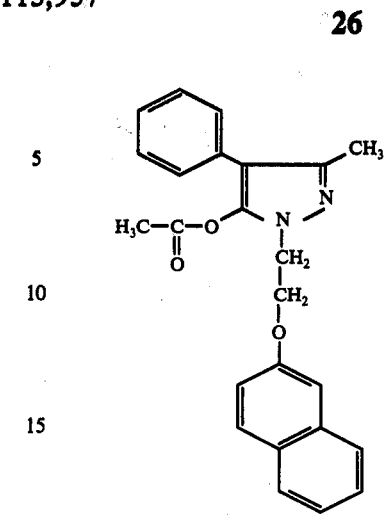

5-Acetoxy-3-methyl-4-phenyl-1-(2-(β-naphthyloxy)-ethyl)-pyrazole was obtained in accordance with the following working instructions:

After addition of 0.11 mol (15.4 g) of calcined potassium carbonate to 0.1 mol (34 g) of 3-methyl-4-phenyl-1-(2-(β-naphthyloxy)-ethyl)-5-pyrazolone in 500 ml of acetone, 0.13 mol (13.5 g) of acetic anhydride were added dropwise.

After heating for 12 hours under reflux, ice water was added to the reaction mixture. The reaction product was extracted with methylene chloride. The extracts were dried with sodium sulphate. After concentrating the solution on a rotary evaporator, the reaction product was obtained in a crystalline form on trituration with petroleum ether. It was recrystallized from methanol.

Melting point: 98°–100° C.

Yield: 84% of theory.

EXAMPLE 18

5-(4-Chlorobenzoyloxy)-3-methyl-4-phenyl-1-(2-(β-naphthyloxy)-ethyl)-5-pyrazole

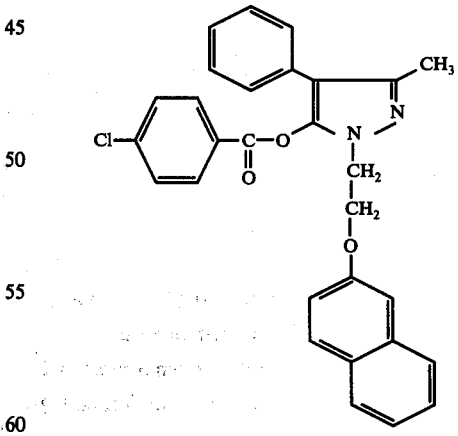

5-(4-Chlorobenzoyloxy)-3-methyl-4-phenyl-1-(2-(β-naphthyloxy)-ethyl)-pyrazole was obtained analogously to the procedure described in Example 17 from 3-methyl-4-phenyl-1-(2-(β-naphthyloxy)-ethyl)-5-pyrazolone and 4-chlorobenzenoic acid anhydride.

Melting point: 109°–111° C (ethanol).

Yield: 91% of theory.

EXAMPLE 19

5-(α-Phenoxy-(n)-butyryloxy)-3-methyl-1-(2-(β-naphthyloxy)-ethyl)-pyrazole

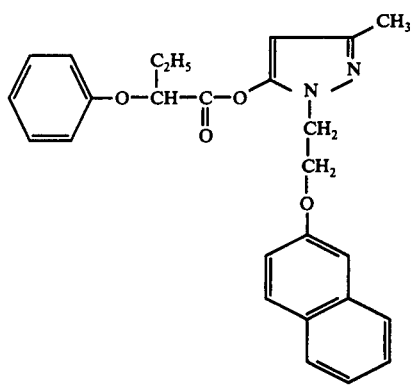

5-(α-Phenoxy-(n)-butyryloxy)-3-methyl-1-(2-(β-naphthyloxy)-ethyl)-pyrazole was obtained analogously to the procedure described in Example 1 from 3-methyl-1-(2-(β-naphthoxy)-ethyl)-5-pyrazolone and α-phenoxybutyric acid chloride.

Melting point: 100°–102° C (ethanol).
Yield: 71% of theory.

EXAMPLE 20

5-(Furyl-(2)-carbonyloxy)-3-methyl-1-(2-(β-naphthyloxy)-ethyl)-pyrazole

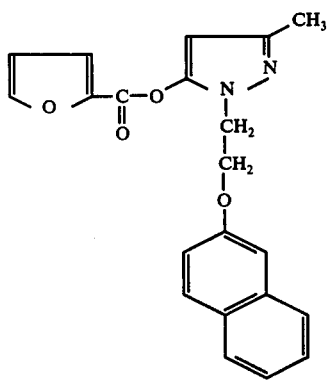

5-(Furyl-(2)-carbonyloxy)-3-methyl-1-(2-(β-naphthyloxy)-ethyl)-pyrazole was obtained analogously to the procedure described in Example 1 from 3-methyl-1-(2-(β-naphthyloxy)-ethyl)-5-pyrazolone and furane-(2)-carboxylic acid chloride.

Melting point: 98°–100° C (ethanol).
Yield: 78% of theory.

EXAMPLE 21

5-(Methylsulphonyloxy)-3-methyl-1-(2-(β-naphthyloxy)-ethyl)-pyrazole

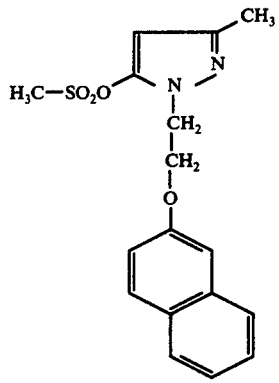

5-(Methylsulphonyloxy)-3-methyl-1-(2-(β-naphthyloxy)-ethyl)-pyrazole was obtained analogously to the procedure described in Example 1 from 3-methyl-1-(2-(β-naphthyloxy)-ethyl)-5-pyrazolone and methanesulphonic acid chloride.

Melting point: 97° – 99° C (methanol).
Yield: 58% of theory.

EXAMPLE 22

5-(Phenylsulphonyloxy)-3-methyl-1-(2-(β-naphthyloxy)-ethyl)-pyrazole 5-(Phenylsulphonyloxy)-3-methyl-1-(2-(β-naphthyloxy)ethyl)-pyrazole was obtained analogously to the procedure described in Example 1 from 3-methyl-1-(2-(β-naphthyloxy)-ethyl)-5-pyrazolone and phenylsulphonic acid chloride.

Melting point: 63° – 65° C (methanol).
Yield: 73% of theory.

EXAMPLE 23

5-(4-Chlorophenylsulphonyloxy)-3-methyl-1-(2-(β-naphthyloxy)-ethyl)-pyrazole

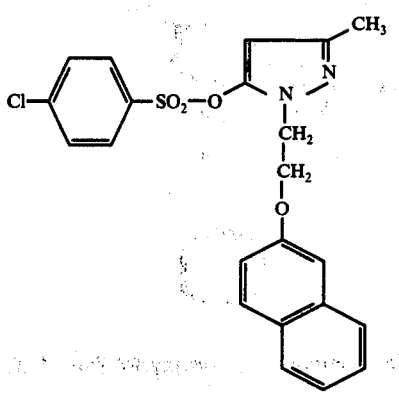

5-(4-Chlorophenylsulphonyloxy)-3-methyl-1-(2-(β-naphthyloxy)-ethyl)-pyrazol was obtained analogously to the procedure described in Example 1 from 3-methyl-1-(2-(β-naphthyloxy)-ethyl)-5-pyrazolone and 4-chlorophenylsulphonic acid chloride.

Melting point: 90° - 92° C (ethanol).

Yield: 75% of theory.

EXAMPLE 24

5-(4-Methylphenylsulphonyloxy)-3-methyl-1-(2-(β-naphthyloxy)-ethyl)-pyrazole

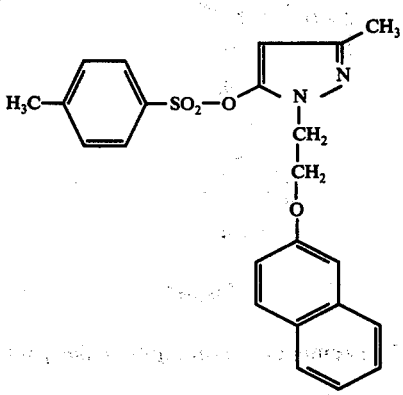

5-(4-Methylphenylsulphenyloxy)-3-methyl-1-(2-(β-naphthyloxy)-ethyl)-pyrazole was obtained analogously to the procedure described in Preparation Example 1 from 3-methyl-1-(2-(β-naphthyloxy)-ethyl)-5-pyrazolone and 4-methylphenylsulphonic acid chloride.

Melting point: 68° - 70° C (methanol).

Yield: 68% of theory.

EXAMPLE 25

5-(2-Methylphenylsulphonyloxy)-3-methyl-1-(2-(β-naphthyloxy)-ethyl)-pyrazole

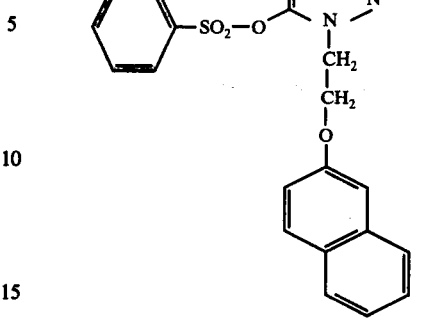

5-(2-Methylphenylsulphonyloxy)-3-methyl-1-(2-(β-naphthyloxy)-ethyl)-pyrazole was obtained analogously to the procedure described in Example 1 from 3-methyl-1-(2-(β-naphthyloxy)-ethyl)-5-pyrazolone and 2-methylphenylsulphonic acid chloride.

Melting point: 74° - 76° C (methanol).

Yield: 63% of theory.

EXAMPLE 26

5-(3,4-Dichlorophenylsulphonyloxy)-3-methyl-1-(2-(β-naphthyloxy)-ethyl)-pyrazole

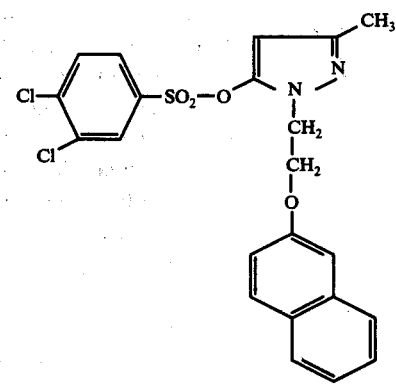

5-(3,4-Dichlorophenylsulphonyloxy)-3-methyl-1-(2-(β-naphthyloxy)-ethyl)-pyrazole was obtained analogously to the procedure described in Example 1 from 3-methyl-1-(2-(β-naphthyloxy)-ethyl)-5-pyrazolone and 3,4-dichlorophenylsulphonic acid chloride.

Melting point: 101° - 103° C (ethanol).

Yield: 82% of theory.

EXAMPLE 27

5-(4-methylbenzoyloxy)-3-methyl-1-benzyl-pyrazole

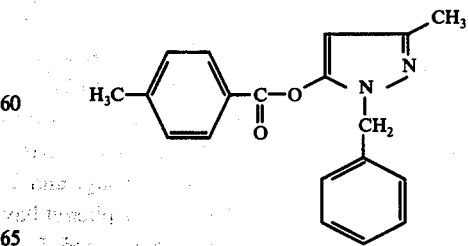

5-(4-methylbenzoyloxy)-3-methyl-1-benzyl-pyrazole was obtained analogously to the procedure described in Example 1 from 3-methyl-1-benzyl-pyrazolone-(5) and 4-methylbenzoylchloride.

Melting point 99° – 101° C (methanol)

Yield: 85% of theory.

What is claimed is:

1. A compound of the formula

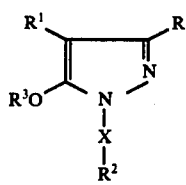

wherein

R is hydrogen, lower alkyl or trifluoromethyl;

$R^1$ is hydrogen or lower alkyl;

$R^3$ is $R^6CO$ wherein $R^6$ is lower alkyl; lower alkyl substituted by phenoxy; lower alkoxy; haloalkyl of 1 to 4 carbon atoms in the alkyl moiety and 1 to 3 halo atoms; cycloalkyl of 5 to 7 carbon atoms; lower alkylthio; haloalkoxy of 1 to 4 carbon atoms in the alkoxy moiety and 1 to 3 halo atoms; haloalkylthio of 1 to 4 carbon atoms in the alkyl moiety and 1 to 3 halo atoms; lower alkoxy(lower alkyl); mono- or di-lower alkylamino(lower akyl); phenyl unsubstituted or substituted by 1 to 3 substituents selected from the group consisting of alkyl of 1 to 4 carbon atoms, alkoxy of 1 to 4 carbon atoms, halo, trifluoromethyl, trifluoromethoxy, nitro, cyano, $SO_n$-alkyl of 1 to 4 carbon atoms in the alkyl moiety and n is 0 to 2, $SO_n$-$CF_3$ wherein n is 0 to 2, carbonamido or sulphonamido;

X is ethylene or ethylene wherein a hydrogen atom on one or both of the carbon atoms is substituted by alkyl of 1 to 4 carbon atoms, linked to $R^2$ via an oxygen or sulphur atom; and $R^2$ is aryl of 6 to 10 carbon atoms unsubstituted or substituted by 1 or 2 substituents selected from the group consisting of lower alkyl, lower alkenyl, lower alkoxy, halo, trifluoromethyl, trifluoromethoxy, cycloalkyl of 5 to 7 carbon atoms, cycloalkenyl of 5 to 7 carbon atoms, nitro, cyano, carboxamido unsubstituted or substituted by 1 or 2 alkyl moieties of 1 to 4 carbon atoms, or by 2 alkylene moieties of 1 to 4 carbon atoms which together with the nitrogen atom form a 5- to 7- membered heterocyclic ring, sulphonamido unsubstituted or substituted by 1 or 2 alkyl moieties of 1 to 4 carbon atoms, or by 2 alkylene moieties of 1 to 4 carbon atoms which together with the nitrogen atom form a 5- to 7-membered heterocyclic ring, and $SO_n$-(lower alkyl) wherein n is 0 to 2; or phenyl having fused thereto a saturated or unsaturated 5- to 7-membered isocyclic ring.

2. The compound according to claim 1 which is

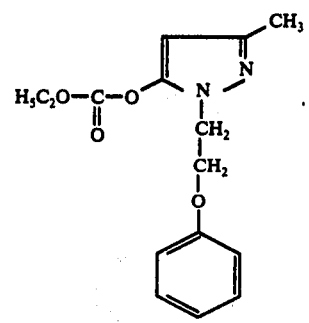

3. The compound according to claim 1 which is

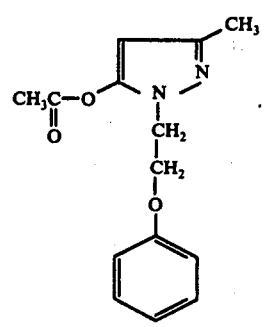

4. The compound according to claim 1 which is

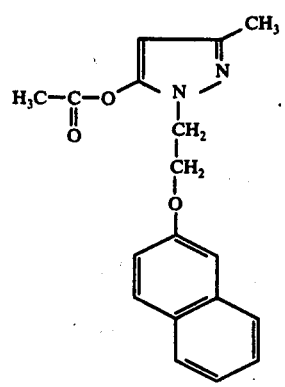

5. The compound according to claim 1 which is

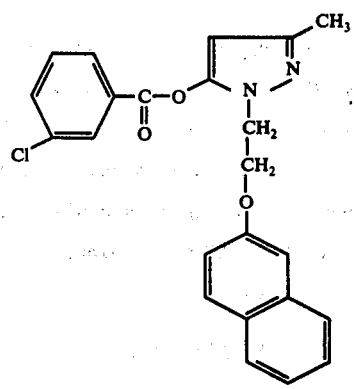

6. The compound according to claim 1 which is

7. The compound according to claim 1 which is
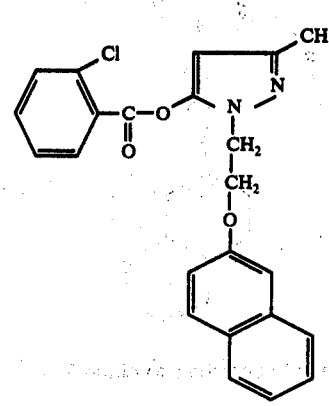
8. The compound according to claim 1 which is
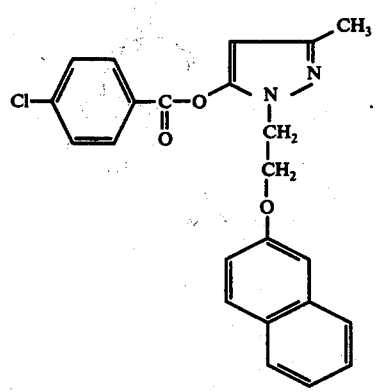
9. The compound according to claim 1 which is
10. The compound according to claim 1 which is
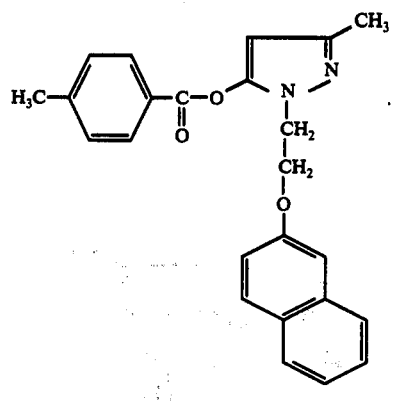
11. The compound according to claim 1 which is
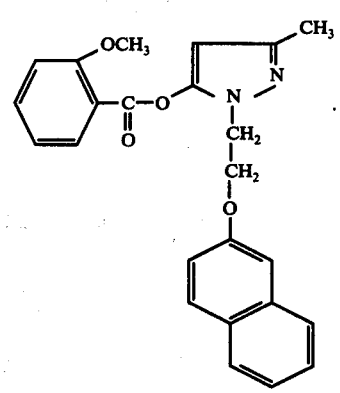
12. The compound according to claim 1 which is
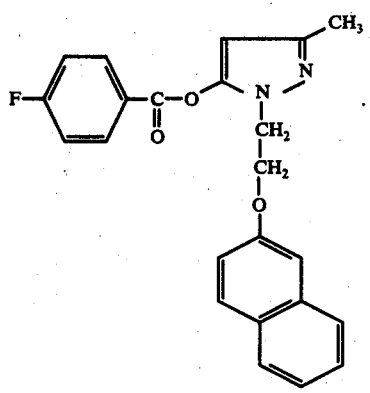
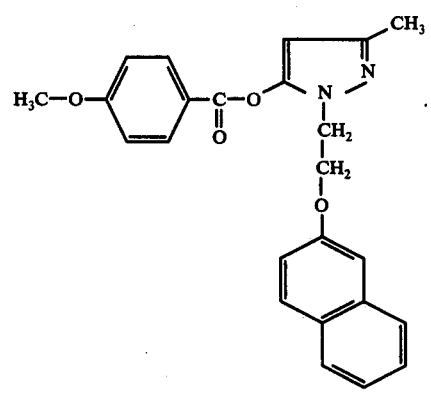

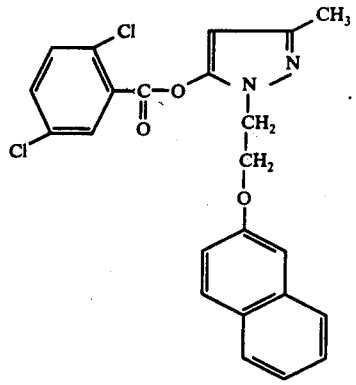
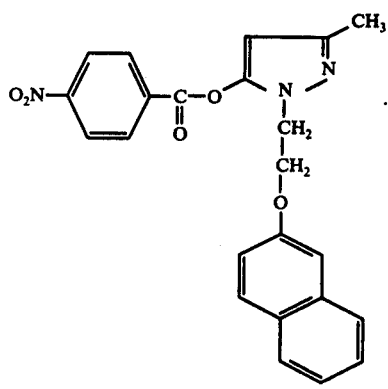
13. The compound according to claim 1 which is
14. The compound according to claim 1 which is
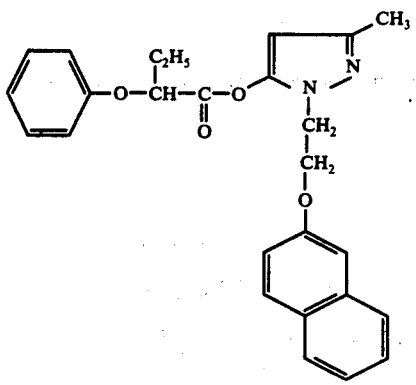
* * * * *